US012735380B2

(12) United States Patent
Choudhary et al.

(10) Patent No.: US 12,735,380 B2
(45) Date of Patent: Sep. 15, 2026

(54) SYNTHESIS OF PARA-ALKYLATED SYRINGYL (METH)ACRYLATE DERIVATIVES AND PHOTOPOLYMERIZABLE COMPOSITIONS FOR ADDITIVE MANUFACTURING IN DENTAL APPLICATIONS

(71) Applicant: Align Technology, Inc., San Jose, CA (US)

(72) Inventors: Umesh Upendra Choudhary, Santa Cruz, CA (US); Jessica Kalay Su, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 801 days.

(21) Appl. No.: 18/091,312

(22) Filed: Dec. 29, 2022

(65) Prior Publication Data

US 2023/0212107 A1 Jul. 6, 2023

Related U.S. Application Data

(60) Provisional application No. 63/295,229, filed on Dec. 30, 2021.

(51) Int. Cl.

| | |
|---|---|
| ***C08F 2/46*** | (2006.01) |
| ***B33Y 70/00*** | (2020.01) |
| ***C07C 67/08*** | (2006.01) |
| ***C07C 69/54*** | (2006.01) |
| ***C08F 2/50*** | (2006.01) |
| ***C08F 220/68*** | (2006.01) |
| ***C08G 61/04*** | (2006.01) |
| *A61C 7/08* | (2006.01) |
| *B33Y 80/00* | (2015.01) |

(52) U.S. Cl.

CPC .............. *C07C 69/54* (2013.01); *B33Y 70/00* (2014.12); *C07C 67/08* (2013.01); *C08F 220/68* (2013.01); *A61C 7/08* (2013.01); *B33Y 80/00* (2014.12); *C07C 2601/16* (2017.05)

(58) Field of Classification Search

CPC ................ C08F 220/302; C08F 220/68; C08F 290/067; C07C 67/08; C07C 69/54; C07C 2601/16; C07C 2601/14; A61C 7/08; A61C 7/002; G16H 50/50; G16H 20/40; G16H 30/40; B33Y 70/00; B33Y 80/00

USPC ....... 522/181, 178, 1, 6, 189, 184, 71; 520/1

See application file for complete search history.

(56) References Cited

U.S. PATENT DOCUMENTS

| | | | |
|---|---|---|---|
| 5,975,893 | A | 11/1999 | Chishti et al. |
| 6,210,162 | B1 | 4/2001 | Chishti et al. |
| 6,309,215 | B1 | 10/2001 | Phan et al. |
| 6,450,807 | B1 | 9/2002 | Chishti et al. |
| 6,497,574 | B1 | 12/2002 | Miller |
| 6,749,414 | B1 | 6/2004 | Hanson et al. |
| 6,830,450 | B2 | 12/2004 | Knopp et al. |
| 6,957,118 | B2 | 10/2005 | Kopelman et al. |
| 6,976,627 | B1 | 12/2005 | Culp et al. |
| 7,092,784 | B1 | 8/2006 | Simkins |
| 7,220,124 | B2 | 5/2007 | Taub et al. |
| 7,236,842 | B2 | 6/2007 | Kopelman et al. |
| 7,245,977 | B1 | 7/2007 | Simkins |
| 7,261,533 | B2 | 8/2007 | Wrosz et al. |
| 7,335,024 | B2 | 2/2008 | Wen |
| 7,384,266 | B2 | 6/2008 | Wen |
| 7,435,084 | B2 | 10/2008 | Liu et al. |
| 7,472,789 | B2 | 1/2009 | Wu et al. |
| 7,476,100 | B2 | 1/2009 | Kuo |
| 7,481,647 | B2 | 1/2009 | Sambu et al. |
| 7,604,181 | B2 | 10/2009 | Culp et al. |
| 7,641,828 | B2 | 1/2010 | DeSimone et al. |
| 7,648,360 | B2 | 1/2010 | Kuo |
| 7,674,422 | B2 | 3/2010 | Kuo |
| 7,711,447 | B2 | 5/2010 | Lu et al. |
| 7,748,199 | B2 | 7/2010 | Sankaran et al. |
| 7,802,987 | B1 | 9/2010 | Phan |
| 7,819,659 | B2 | 10/2010 | Wen |
| 7,831,322 | B2 | 11/2010 | Liu et al. |
| 7,840,373 | B2 | 11/2010 | Culp et al. |
| 7,892,474 | B2 | 2/2011 | Shkolnik et al. |
| 7,922,490 | B2 | 4/2011 | Wen |
| 7,957,824 | B2 | 6/2011 | Boronvinskih et al. |
| 8,019,465 | B2 | 9/2011 | Spiridonov et al. |
| 8,030,588 | B2 | 10/2011 | Culp et al. |

(Continued)

FOREIGN PATENT DOCUMENTS

| | | |
|---|---|---|
| JP | 2003084390 A | 3/2003 |
| JP | 2011215413 A | 10/2011 |

(Continued)

OTHER PUBLICATIONS

Jensen, J.J., "Adamantyl Substituted Polymers," Dissertation University of Southern Mississippi, 1997, 24 pages. Retrieved from the Internet: URL:https://www.proquest.com/dissertations- theses/adamantyl-substituted-polymers-dip henylethynyl/docview/304371551/se-2.

(Continued)

*Primary Examiner* — Jessica Whiteley

(74) *Attorney, Agent, or Firm* — Seed Intellectual Property Law Group LLP

(57) ABSTRACT

The present disclosure provides polymerizable monomers which may be used as reactive diluents in additive manufacturing. The polymerizable monomers may have low vapor pressures and may be compatible with a range of low glass transition temperature oligomers.

20 Claims, 8 Drawing Sheets

(56) References Cited

U.S. PATENT DOCUMENTS

| | | | |
|---|---|---|---|
| 8,087,932 | B2 | 1/2012 | Liu |
| 8,636,513 | B2 | 1/2014 | Wen |
| 8,765,031 | B2 | 7/2014 | Li et al. |
| 8,776,391 | B1 | 7/2014 | Kaza et al. |
| 9,108,338 | B2 | 8/2015 | Sirovskiy et al. |
| 9,403,238 | B2 | 8/2016 | Culp |
| 9,943,386 | B2 | 4/2018 | Webber et al. |
| 9,943,991 | B2 | 4/2018 | Tanugula et al. |
| 10,336,102 | B2 | 7/2019 | Cole |
| 10,495,973 | B2 | 12/2019 | Cole |
| 10,783,629 | B2 | 9/2020 | Parpara et al. |
| 10,888,395 | B2 | 1/2021 | Kopelman |
| 11,189,021 | B2 | 11/2021 | Shah et al. |
| 11,295,444 | B2 | 4/2022 | Cherkas et al. |
| 11,420,362 | B2 | 8/2022 | Mojdeh et al. |
| 11,511,485 | B2 | 11/2022 | Mojdeh et al. |
| 11,534,277 | B2 | 12/2022 | Chavez et al. |
| 11,602,413 | B2 | 3/2023 | Chen et al. |
| 11,666,415 | B2 | 6/2023 | Wang et al. |
| 2004/0243361 | A1 | 12/2004 | Steuben et al. |
| 2006/0093982 | A1 | 5/2006 | Wen |
| 2006/0093987 | A1 | 5/2006 | Wen |
| 2006/0093993 | A1 | 5/2006 | Wen |
| 2006/0127850 | A1 | 6/2006 | Wen |
| 2006/0127857 | A1 | 6/2006 | Zhenhuan et al. |
| 2006/0127858 | A1 | 6/2006 | Wen |
| 2006/0127859 | A1 | 6/2006 | Wen |
| 2006/0127860 | A1 | 6/2006 | Wen |
| 2006/0172250 | A1 | 8/2006 | Wen |
| 2006/0199145 | A1 | 9/2006 | Liu et al. |
| 2007/0092853 | A1 | 4/2007 | Liu et al. |
| 2007/0243502 | A1 | 10/2007 | Wen |
| 2008/0083348 | A1 | 4/2008 | Kuo et al. |
| 2009/0148814 | A1 | 6/2009 | Li et al. |
| 2014/0061974 | A1 | 3/2014 | Tyler |
| 2014/0265034 | A1 | 9/2014 | Dudley |
| 2015/0097315 | A1 | 4/2015 | DeSimone et al. |
| 2015/0097316 | A1 | 4/2015 | DeSimone et al. |
| 2015/0102532 | A1 | 4/2015 | DeSimone et al. |
| 2016/0024279 | A1* | 1/2016 | Matsushima ............. C08F 2/48 252/79 |
| 2017/0015775 | A1* | 1/2017 | Holmberg ............... C07C 69/54 |
| 2020/0290262 | A1 | 9/2020 | Aguilar Mendez et al. |
| 2021/0030516 | A1 | 2/2021 | O'Leary et al. |
| 2022/0380502 | A1* | 12/2022 | Choudhary ............ A61C 7/002 |

FOREIGN PATENT DOCUMENTS

| | | | |
|---|---|---|---|
| WO | WO-2015075094 | A1 | 5/2015 |
| WO | WO-2016078838 | A1 | 5/2016 |
| WO | WO-2018032022 | A1 | 2/2018 |
| WO | 2020104873 | A1 | 5/2020 |
| WO | 2021178363 | A1 | 9/2021 |

OTHER PUBLICATIONS

Tumbleston, et al., "Additive Manufacturing. Continuous Liquid Interface Production of 3D Objects," Science (New York, N.Y.), 2015, vol. 347(6228), pp. 1349-1352.

* cited by examiner

Vertical Dimension

Lateral Dimensions

SYNTHESIS OF PARA-ALKYLATED SYRINGYL (METH)ACRYLATE DERIVATIVES AND PHOTOPOLYMERIZABLE COMPOSITIONS FOR ADDITIVE MANUFACTURING IN DENTAL APPLICATIONS

CROSS-REFERENCE TO RELATED APPLICATION

The present application claims the benefit of U.S. Provisional Patent Application No. 63/295,229, filed Dec. 30, 2021, which is incorporated herein by reference in its entirety.

BACKGROUND OF THE INVENTION

Balancing resin properties and evaporation during polymer printing is a central challenge in many areas of additive manufacturing. While diluents can impart desirable properties upon resins, including low viscosities suitable for manufacturing, such diluents often have high vapor pressures, and thus render compositions time-variant and unsuitable for printing.

SUMMARY OF THE INVENTION

Various aspects of the present disclosure provide a compound having the structure of Formula (I), or a salt or solvate thereof:

(I)

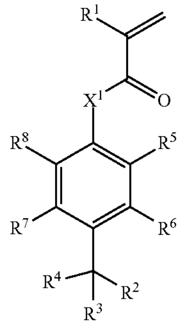

wherein:

$R^1$ is H, halogen, $C_1$-$C_6$ alkyl, $C_1$-$C_6$ alkenyl, $C_1$-$C_6$ alkynyl, $C_1$-$C_6$ cycloalkyl, $C_1$-$C_6$ heterocycloalkyl, —$OR^9$, or —$N(R^9)_2$;

each instance of $R^2$, $R^3$, and $R^4$ is independently selected from the group consisting of $C_1$-$C_6$ alkyl, $C_1$-$C_6$ alkenyl, $C_1$-$C_6$ alkynyl, $C_1$-$C_6$ cycloalkyl, $C_1$-$C_6$ heterocycloalkyl, —$OR^9$, and —$N(R^9)_2$; or optionally any two of $R^2$, $R^3$, and $R^4$ are taken together along with the carbon to which they are commonly attached to form $C_1$-$C_6$ cycloalkyl or $C_1$-$C_6$ heterocycloalkyl; or optionally $R^2$, $R^3$, and $R^4$ are taken together along with the carbon to which they are commonly attached to form a caged ring;

$R^5$, $R^6$, $R^7$, and $R^8$ are each independently selected from the group consisting of halogen, $C_1$-$C_6$ alkyl, $C_1$-$C_6$ alkenyl, $C_1$-$C_6$ alkynyl, —$OR^9$, —$N(R^9)_2$, —(C═O)—$R^9$, —O—(C═O)—$R^9$, and —$(NR^9)$—(C═O)—$R^9$;

each instance of $R^9$ is independently selected from the group consisting of H, $C_1$-$C_6$ alkyl, $C_1$-$C_6$ alkenyl, and $C_1$-$C_6$ alkynyl;

each instance of $R^1$, $R^2$, $R^3$, $R^4$, $R^5$, $R^6$, $R^7$, and $R^8$ is independently optionally substituted with one or more instances of $R^{10}$;

each instance of $R^{10}$ is independently selected from the group consisting of ═O, halogen, $C_1$-$C_4$ alkyl, $C_1$-$C_4$ alkenyl, $C_1$-$C_4$ alkynyl, —$OR^9$, —$N(R^9)_2$, —(C═O)—$R^9$, —O—(C═O)—$R^9$, and —$(NR^9)$—(C═O)—$R^9$; and $X^1$ is $C(R^9)_2$, $NR^9$, O, or S.

In some embodiments, the compound comprises a single polymerizable olefin. In some embodiments, $R^1$ is H, $C_1$-$C_6$ alkyl, $C_1$-$C_6$ alkenyl, or $C_1$-$C_6$ alkynyl, $C_1$-$C_6$ cycloalkyl, or $C_1$-$C_6$ heterocycloalkyl. In some embodiments, each instance of $R^2$, $R^3$, and $R^4$ is independently selected from the group consisting of $C_1$-$C_6$ alkyl, $C_1$-$C_6$ alkenyl, or $C_1$-$C_6$ alkynyl. In some embodiments, $R^2$, $R^3$, and $R^4$ are taken together along with the carbon to which they are commonly attached to form a caged ring. In some embodiments, $R^2$, $R^3$, and $R^4$ are taken together along with the carbon to which they are commonly attached to form

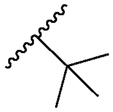 , 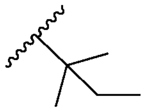 , 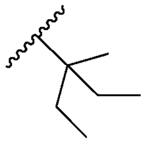 ,

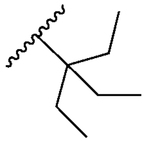 , 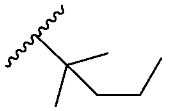 ,

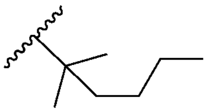 , 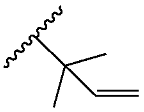 ,

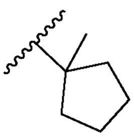 , 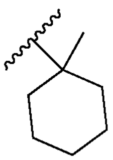 , 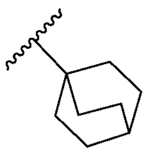 ,

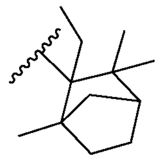 , or 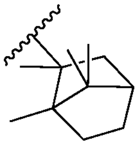 .

In some embodiments, $R^5$, $R^6$, $R^7$, and $R^8$ are each H or —$OR^9$. In some embodiments, $R^6$ and $R^7$ are H. In some embodiments, $X^1$ is O.

In some embodiments, the compound comprises a structure of Formula (Ib):

(Ib)

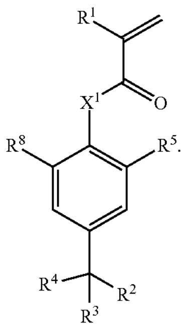

In some embodiments, the compound comprises the compound is liquid or crystalline at room temperature and 1 atmosphere pressure. In some embodiments, the compound comprises a vapor pressure of less than 500 pascals (Pa) at 60° C.

Various aspects of the present disclosure provide a composition comprising a compound of any one of claims 1-12 and an oligomer comprising a low glass transition temperature ($T_g$). In some embodiments, the composition comprises between about 10% and about 50% of the oligomer by weight. In some embodiments, the composition comprises between about 40% and 80% of the compound of any one of claims 1-12 by weight. In some embodiments, the composition comprises a crosslinker. In some embodiments, the crosslinker comprises polytetrahydrofuran (PTHF), 1,4-cyclohexane-dimethanol-based polycarbonate, or a derivative thereof. In some embodiments, the crosslinker comprises PTHF. In some embodiments, the crosslinker comprises 1,4-cyclohexane-dimethanol-based polycarbonate. In some embodiments, the composition comprises between about 4% and 16% of the crosslinker. In some embodiments, the compositions comprises a photoinitiator. In some embodiments, upon curing the composition comprises at least one property selected from the group consisting of: (i) a Young's modulus at 1.7 mm/min of between 800 and 1500 megapascals (MPa); (ii) a Young's modulus at 510 mm/min of between 1200 and 2000 MPa; (iii) an elongation at break at 1.7 mm/min of between 60% and 200%; (iv) an elongation at break at 510 mm/min of between 10% and 120%; (v) a yield stress at 1.7 mm/min of between 24 and 35 MPa; (vi) a yield stress at 510 mm/min of between 35 and 55 MPa; (vii) a 24 hour force of between 1.3 and 3.0 Newtons (N); and (viii) a glass transition temperature of between 90 and 160° C.

Various aspects of the present disclosure provide a method for synthesizing a compound having the structure of Formula (I), the method comprising coupling

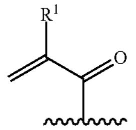

to a phenol hydroxyl, a thiophenol thiol, or an aniline amine. In some embodiments, the method comprises alkylating the phenol, the thiophenol, or the aniline, wherein the alkylating comprises coupling —$CR^2R^3R^4$ to the phenol, the thiophenol, or the aniline aryl.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DESCRIPTION OF THE FIGURES

The novel features of the invention are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

DETAILED DESCRIPTION OF THE INVENTION

Figure 1A:
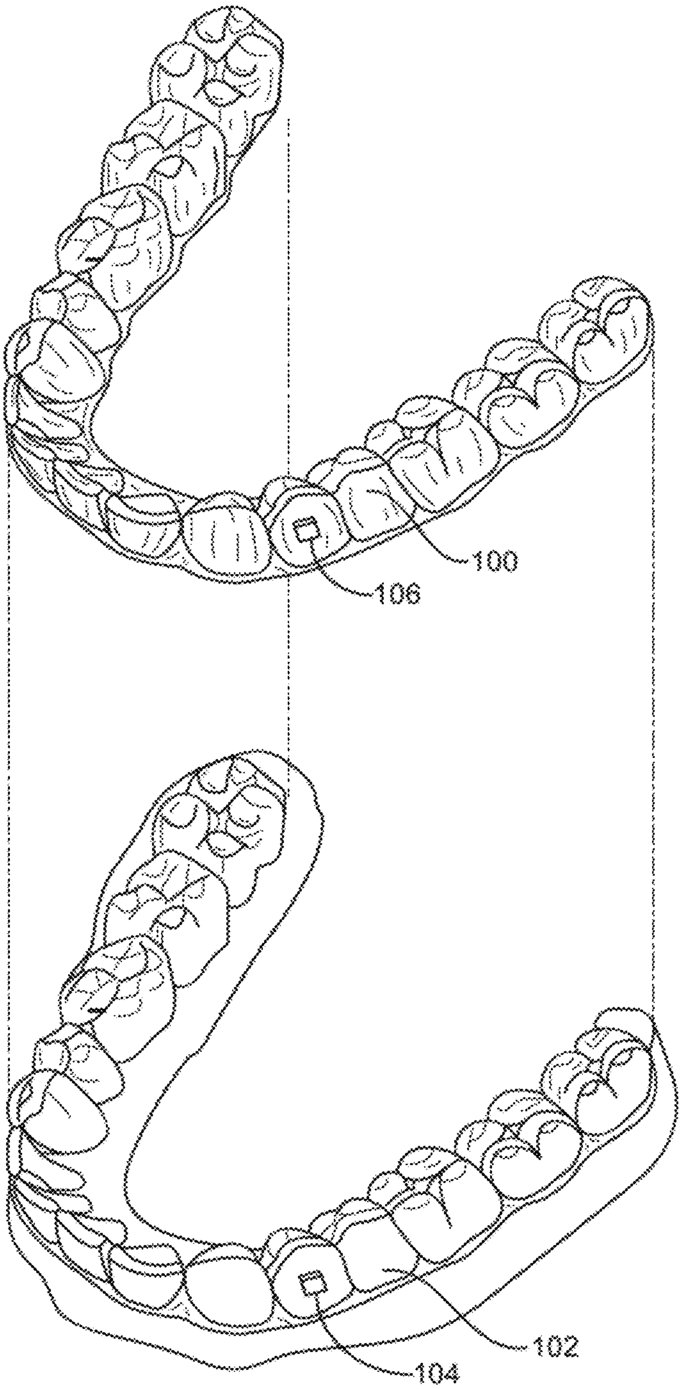
FIG. 1A illustrates a tooth repositioning appliance, in accordance with embodiments.

Pursuant to the need for low vapor pressure reactive diluents for additive manufacturing, the present disclosure provides polymerizable monomers suitable for use in curable resins. The polymerizable monomers may comprise acrylate, methacrylate, and related polymerizable olefins coupled to alkyl substituted phenyls which can impart low vapor pressures while maintaining desired viscosities, miscibility, and physical properties upon polymerization. In many cases, the polymerizable monomers are monofunctional, such that the polymerizable monomers do not affect crosslinking in curable resins.

Further disclosed herein are curable resins comprising polymerizable monomers of the present disclosure. In some cases, the curable resins comprise at least 50% by weight of the polymerizable monomers. The curable resins can further comprise a polymerizable oligomer or polymer, which may have a low glass transition temperature (Tg) suitable for additive manufacturing. The curable resins can be photo-curable, thermo-curable, chemically-curable, or any combination thereof. The curable resins may be used in the manufacture of objects, such as orthodontic devices.

I. Definitions

All terms, chemical names, expressions, and designations have their usual meanings which are well-known to those skilled in the art. As used herein, the terms "to comprise" and "comprising" are to be understood as non-limiting, i.e., other components than those explicitly named may be included.

Number ranges are to be understood as inclusive, i.e., including the indicated lower and upper limits. Furthermore, the term "about", as used herein, and unless clearly indicated otherwise, generally refers to and encompasses plus or minus 10% of the indicated numerical value(s). For example, "about 10%" may indicate a range of 9% to 11%, and "about 1" may include the range 0.9-1.1.

As used herein, the term "polymer" generally refers to a molecule composed of repeating structural units connected by covalent chemical bonds and characterized by a substantial number of repeating units (e.g., equal to or greater than 20 repeating units and often equal to or greater than 100 repeating units and often equal to or greater than 200 repeating units) and a molecular weight greater than or equal to 5,000 Daltons (Da) or 5 kDa, such as greater than or equal to 10 kDa, 15 kDa, 20 kDa, 30 kDa, 40 kDa, 50 kDa, or 100 kDa. Polymers are commonly the polymerization product of one or more monomer precursors. The term polymer includes homopolymers, i.e., polymers consisting essentially of a single repeating monomer species. The term polymer also includes copolymers which are formed when two or more different types (or species) of monomers are linked in the same polymer. Copolymers may comprise two or more different monomer species, and include random, block, alternating, segmented, grafted, tapered and other copolymers. The term "cross-linked polymers" generally refers to polymers having one or multiple links between at least two polymer chains, which can result from multivalent monomers forming cross-linking sites upon polymerization. In various embodiments, a polymer herein is a telechelic polymer capable of undergoing further polymerization reactions, e.g., with other polymerizable components present in a curable composition.

As used herein, the term "oligomer" generally refers to a molecule composed of repeating structural units connected by covalent chemical bonds and characterized by a number of repeating units less than that of a polymer (e.g., equal to or less than 20 or less than 10 repeating units) and a lower molecular weight than polymers, e.g., less than 5,000 Da or less than 2,000 Da, and in various cases from about 0.5 kDa to about 5 kDa. In some cases, oligomers may be the polymerization product of one or more monomer precursors. In various embodiments, an oligomer herein is a telechelic oligomer capable of undergoing further polymerization reactions, e.g., with other polymerizable components present in a curable composition.

As used herein, the terms "telechelic polymer" and "telechelic oligomer" generally refer to a polymer or oligomer, the molecules of which are capable of entering, through polymerizable reactive functional groups, into further polymerization.

As used herein, the term "reactive diluent" generally refers to a substance which reduces the viscosity of another substance, such as a monomer or curable resin. A reactive diluent may become part of another substance, such as a polymer obtained by a polymerization process. In some examples, a reactive diluent is a curable monomer which, when mixed with a curable resin, reduces the viscosity of the resultant formulation and is incorporated into the polymer that results from polymerization of the formulation.

Oligomer and polymer mixtures can be characterized and differentiated from other mixtures of oligomers and polymers by measurements of molecular weight and molecular weight distributions.

The average molecular weight (M) is the average number of repeating units n times the molecular weight or molar mass ($M_i$) of the repeating unit. The number-average molecular weight (Mn) is the arithmetic mean, representing the total weight of the molecules present divided by the total number of molecules.

Photoinitiators described in the present disclosure can include those that can be activated with light and initiate polymerization of the polymerizable components of a resin or formulation. A "photoinitiator", as used herein, may generally refer to a compound that can produce radical species and/or promote radical reactions upon exposure to radiation (e.g., UV or visible light).

The term "biocompatible," as used herein, refers to a material that does not elicit an immunological rejection or detrimental effect, referred herein as an adverse immune response, when it is disposed within an in-vivo biological environment. For example, in embodiments a biological marker indicative of an immune response changes less than 10%, or less than 20%, or less than 25%, or less than 40%, or less than 50% from a baseline value when a human or animal is exposed to or in contact with the biocompatible material. Alternatively, immune response may be determined histologically, wherein localized immune response is assessed by visually assessing markers, including immune cells or markers that are involved in the immune response pathway, in and adjacent to the material. In an aspect, a biocompatible material or device does not observably change immune response as determined histologically. In some embodiments, the disclosure provides biocompatible devices configured for long-term use, such as on the order of weeks to months, without invoking an adverse immune response. Biological effects may be initially evaluated by measurement of cytotoxicity, sensitization, irritation and intracutaneous reactivity, acute systemic toxicity, pyrogenicity, subacute/subchronic toxicity and/or implantation. Biological tests for supplemental evaluation include testing for chronic toxicity.

"Bioinert" refers to a material that does not elicit an immune response from a human or animal when it is disposed within an in-vivo biological environment. For example, a biological marker indicative of an immune response remains substantially constant (plus or minus 5% of a baseline value) when a human or animal is exposed to or in contact with the bioinert material. In some embodiments, the disclosure provides bioinert devices.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individually or in any combination. Additionally, unless otherwise specified, all isotopic variants of compounds disclosed herein are intended to be encompassed by the disclosure. Specific names of compounds are intended to be exemplary, as it is known that one of ordinary skill in the art can name the same compounds differently.

It is noted that as used herein and in the appended claims, the singular forms "a", "an", and "the" include plural reference unless the context clearly dictates otherwise. Thus, for example, reference to "a monomer" includes a plurality of such monomers and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim.

As used herein, the term "group" may refer to a reactive functional group of a chemical compound. Groups of the present compounds refer to an atom or a collection of atoms that are a part of the compound. Groups of the present disclosure may be attached to other atoms of the compound via one or more covalent bonds. Groups may also be characterized with respect to their valence state. The present disclosure includes groups characterized as monovalent, divalent, trivalent, etc. valence states.

As used herein, the term "substituted" refers to a compound (e.g., an alkyl chain) wherein a hydrogen is replaced by another reactive functional group or atom, as described herein.

As used herein, a broken line in a chemical structure can be used to indicate a bond to the rest of the molecule. For example,

 in 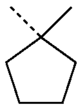

in is used to designate the 1-position as the point of attachment of 1-methylcyclopentate to the rest of the molecule. Alternatively,

 in, e.g., 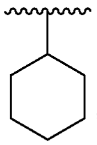, can be used to indicate that the given moiety, the cyclohexyl moiety in this example, is attached to a molecule via the bond that is "capped" with the wavy line.

Alkyl groups include straight-chain, branched and cyclic alkyl groups, unless otherwise defined for a compound or genus of compounds. Alkyl groups include those having from 1-30 carbon atoms, unless otherwise defined. Thus, alkyl groups can include small alkyl groups having from 1-3 carbon atoms, medium length alkyl groups having from 4-10 carbon atoms, as well as long alkyl groups having more than 10 carbon atoms, particularly those having 10-30 carbon atoms. The term cycloalkyl specifically refers to an alkyl group having a ring structure such as a ring structure comprising 3-30 carbon atoms, optionally 3-20 carbon atoms and optionally 3-10 carbon atoms, including an alkyl group having one or more rings. Cycloalkyl groups include those having a 3-, 4-, 5-, 6-, 7-, 8-, 9-, or 10-membered carbon ring(s) and particularly those having a 3-, 4-, 5-, 6-, 7-, or 8-membered ring(s). The carbon rings in cycloalkyl groups can also carry alkyl groups. Cycloalkyl groups can include bicyclic and tricyclic alkyl groups. Alkyl groups are optionally substituted, as described herein. Substituted alkyl groups can include among others those which are substituted with aryl groups, which in turn can be optionally substituted. Specific alkyl groups include methyl, ethyl, n-propyl, isopropyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Unless otherwise defined herein, substituted alkyl groups include fully halogenated or semihalogenated alkyl groups, such as alkyl groups having one or more hydrogens replaced with one or more fluorine atoms, chlorine atoms, bromine atoms and/or iodine atoms. Thus, substituted alkyl groups can include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alkyl portion of the groups is substituted as provided herein in connection with the description of alkyl groups. As used herein MeO— refers to $CH_3O$—. Moreover, a thioalkoxy group, as used herein is an alkyl group that has been modified by linkage to sulfur atom (instead of an oxygen) and can be represented by the formula R—S.

Alkenyl groups include straight-chain, branched and cyclic alkenyl groups. Alkenyl groups include those having 1, 2 or more double bonds and those in which two or more of the double bonds are conjugated double bonds. Unless otherwise defined herein, alkenyl groups include those having from 2-20 carbon atoms. Alkenyl groups include small alkenyl groups having from 2-3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9-, or 10-membered carbon ring(s) and particularly those having a 3-, 4-, 5-, 6-, 7- or 8-, membered ring(s). The carbon rings in cycloalkenyl groups can also carry alkyl groups. Cycloalkenyl groups can include bicyclic and tricyclic alkenyl groups. Alkenyl groups are optionally substituted. Unless otherwise defined herein, substituted alkenyl groups include among others those that are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, and cyclohexenyl, all of which are optionally substituted. Substituted alkenyl groups can include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6-, 7- or 8-membered aromatic rings, including heterocyclic aromatic rings. The term heteroaryl specifically refers to aryl groups having at least one 5-, 6-, 7- or 8-member heterocyclic aromatic ring. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those that are substituted with alkyl or alkenyl groups, which groups in turn can be optionally substituted. Specific aryl groups include phenyl, biphenyl, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein provided in a covalently bonded configuration in the compounds of the disclosure at any suitable point of attachment. In some embodiments, aryl groups contain between 5 and 30 carbon atoms. In some embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As used herein, the terms "alkylene" and "alkylene group" are used synonymously and refer to a divalent group "$—CH_2—$" derived from an alkyl group as defined herein. The disclosure includes compounds having one or more alkylene groups. Alkylene groups in some compounds function as attaching and/or spacer groups. Compounds of the disclosure may have substituted and/or unsubstituted $C_1$-$C_{20}$ alkylene, $C_1$-$C_{10}$ alkylene and $C_1$-$C_6$ alkylene groups.

As used herein, the terms "cycloalkylene" and "cycloalkylene group" are used synonymously and refer to a divalent group derived from a cycloalkyl group as defined herein. The disclosure includes compounds having one or more cycloalkylene groups. Cycloalkyl groups in some compounds function as attaching and/or spacer groups. Compounds of the disclosure may have substituted and/or unsubstituted $C_3$-$C_{20}$ cycloalkylene, $C_3$-$C_{10}$ cycloalkylene and $C_3$-$C_5$ cycloalkylene groups.

As used herein, the terms "arylene" and "arylene group" are used synonymously and refer to a divalent group derived from an aryl group as defined herein. The disclosure includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorophore, aromatic antenna, dye and/or imaging groups. Compounds of the disclosure include substituted and/or unsubstituted $C_5$-$C_{30}$ arylene, $C_5$-$C_{20}$ arylene, $C_5$-$C_{10}$ arylene and $C_5$-$C_8$ arylene groups.

As used herein, the terms "heteroarylene" and "heteroarylene group" are used synonymously and refer to a divalent group derived from a heteroaryl group as defined herein. The disclosure includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorophore, dye and/or imaging groups. Compounds of the disclosure include substituted and/or unsubstituted $C_5$-$C_{30}$ heteroarylene, $C_5$-$C_{20}$ heteroarylene, $C_5$-$C_{10}$ heteroarylene and $C_5$-$C_8$ heteroarylene groups.

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as attaching and/or spacer groups. Compounds of the disclosure include substituted and/or unsubstituted $C_2$-$C_{20}$ alkenylene, $C_2$-$C_{10}$ alkenylene and $C_2$-$C_5$ alkenylene groups.

As used herein, the terms "cycloalkenylene" and "cycloalkenylene group" are used synonymously and refer to a divalent group derived from a cycloalkenyl group as defined herein. The disclosure includes compounds having one or more cycloalkenylene groups. Cycloalkenylene groups in some compounds function as attaching and/or spacer groups. Compounds of the disclosure include substituted and/or unsubstituted $C_3$-$C_{20}$ cycloalkenylene, $C_3$-$C_{10}$ cycloalkenylene and $C_3$-$C_5$ cycloalkenylene groups.

As used herein, the terms "alkynylene" and "alkynylene group" are used synonymously and refer to a divalent group derived from an alkynyl group as defined herein. The disclosure includes compounds having one or more alkynylene groups. Alkynylene groups in some compounds function as attaching and/or spacer groups. Compounds of the disclosure include substituted and/or unsubstituted $C_2$-$C_{20}$ alkynylene, $C_2$-$C_{10}$ alkynylene and $C_2$-$C_5$ alkynylene groups.

As used herein, the terms "halo" and "halogen" can be used interchangeably and refer to a halogen group such as a fluoro (—F), chloro (—Cl), bromo (—Br) or iodo (—I).

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and reactive functional groups, for example, provided as substituents.

The term "carbocyclic" refers to ring structures containing only carbon atoms in the ring. Carbon atoms of carbocyclic rings can be bonded to a wide range of other atoms and reactive functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, e.g., 1 to 4, and in some embodiments 1 to 3.

The term "heteroalkyl", as used herein, generally refers to an alkyl, alkenyl or alkynyl group as defined herein, wherein at least one carbon atom of the alkyl group is replaced with a heteroatom. In some instances, heteroalkyl groups may contain from 1 to 18 non-hydrogen atoms (carbon and heteroatoms) in the chain, or from 1 to 12 non-hydrogen atoms, or from 1 to 6 non-hydrogen atoms, or from 1 to 4 non-hydrogen atoms. Heteroalkyl groups may be straight or branched, and saturated or unsaturated. Unsaturated heteroalkyl groups have one or more double bonds and/or one or more triple bonds. Heteroalkyl groups may be unsubstituted or substituted. Exemplary heteroalkyl groups include, but are not limited to, alkoxyalkyl (e.g., methoxymethyl), and aminoalkyl (e.g., alkylaminoalkyl and dialkylaminoalkyl). Heteroalkyl groups may be optionally substituted with one or more substituents.

The term "carbonyl", as used herein, for example in the context of $C_{1-6}$ carbonyl substituents, generally refers to a carbon chain of given length (e.g., $C_{1-6}$), wherein each of the carbon atom of a given carbon chain can form the carbonyl bond, as long as it chemically feasible in terms of the valence state of that carbon atom. Thus, in some instance, the "$C_1$-6 carbonyl" substituent refers to a carbon chain of between 1 and 6 carbon atoms, and either the terminal carbon contains the carbonyl functionality, or an inner carbon contains the carbonyl functionality, in which case the substituent could be described as a ketone. The term "carboxy", as used herein, for example in the context of $C_{1-6}$ carboxyl substituents, generally refers to a carbon chain of given length (e.g., $C_{1-6}$), wherein a terminal carbon contains the carboxy functionality, unless otherwise defined herein.

As to any of the groups described herein that contain one or more substituents, it is understood that such groups do not contain any substitution or substitution patterns which are sterically impractical and/or synthetically non-feasible. In addition, the compounds of this disclosure include all stereochemical isomers arising from the substitution of these compounds.

Unless otherwise defined herein, optional substituents for any alkyl, alkenyl and aryl group includes substitution with one or more of the following substituents, among others:

halogen, including fluorine, chlorine, bromine or iodine;

pseudohalides, including —CN, —OCN (cyanate), —NCO (isocyanate), —SCN (thiocyanate) and —NCS (isothiocyanate);

—COOR, where R is a hydrogen or an alkyl group or an aryl group and more specifically where R is a methyl, ethyl, propyl, butyl, or phenyl group all of which groups are optionally substituted;

—COR, where R is a hydrogen or an alkyl group or an aryl group and more specifically where R is a methyl, ethyl, propyl, butyl, or phenyl group all of which groups are optionally substituted;

—CON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$, where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring that can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—$SO_2R$, or —SOR, where R is an alkyl group or an aryl group and more specifically where R is a methyl, ethyl, propyl, butyl, or phenyl group, all of which are optionally substituted;

—OCOOR, where R is an alkyl group or an aryl group;

—$SO_2N(R)_2$, where each R, independently of each other R, is a hydrogen, or an alkyl group, or an aryl group all of which are optionally substituted and wherein R and R can form a ring that can contain one or more double bonds and can contain one or more additional carbon atoms; and —OR, where R is H, an alkyl group, an aryl group, or an acyl group all of which are optionally substituted. In a particular example R can be an acyl yielding —OCOR", wherein R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups that contain one or more substituents, it is understood that such groups do not contain any substitution or substitution patterns which are sterically impractical and/or synthetically non-feasible. In addition, as further described herein, the compounds of this disclosure can include all stereochemical isomers (and racemic mixtures) arising from the substitution of these compounds.

II. Polymerizable Monomers

A curable resin of the present disclosure can comprise one or more species of polymerizable monomers. Such polymerizable monomers can be used as reactive diluents. In various cases, a polymerizable monomer can comprise an acrylate, methacrylate, acrylamide, methacrylamide, thioacrylate, methylthioacrylate, or vinyl ketone moiety for incorporation into an oligomeric or polymeric backbone, coupled to a linear or cyclic (e.g., mono-, bi-, or tricyclic) side-chain moiety. Generally, any aliphatic, cycloaliphatic, or aromatic molecule with a mono-functional polymerizable reactive functional group can be used (also includes liquid crystalline monomers). In some instances, the polymerizable reactive functional groups are acrylate or methacrylate groups. A reactive diluent used herein can have a low vapor pressure as further described below.

In various embodiments, a polymerizable monomer herein comprises a structure according to Formula (I):

(I)

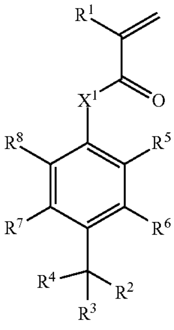

wherein $R^1$ is H, halogen, $C_1$-$C_6$ alkyl, $C_1$-$C_6$ alkenyl, $C_1$-$C_6$ alkynyl, $C_1$-$C_6$ cycloalkyl, $C_1$-$C_6$ heterocycloalkyl, —$OR^9$, or —$N(R^9)_2$;

each instance of $R^2$, $R^3$, and $R^4$ is independently selected from the group consisting of $C_1$-$C_6$ alkyl, $C_1$-$C_6$ alkenyl, $C_1$-$C_6$ alkynyl, $C_1$-$C_6$ cycloalkyl, $C_1$-$C_6$ heterocycloalkyl, —$OR^9$, and —$N(R^9)_2$; or optionally any two of $R^2$, $R^3$, and $R^4$ are taken together along with the carbon to which they are commonly attached to form $C_1$-$C_6$ cycloalkyl or $C_1$-$C_6$ heterocycloalkyl; or optionally $R^2$, $R^3$, and $R^4$ are taken together along with the carbon to which they are commonly attached to form a caged ring;

$R^5$, $R^6$, $R^7$, and $R^8$ are each independently selected from the group consisting of H, halogen, $C_1$-$C_6$ alkyl, $C_1$-$C_6$ alkenyl, $C_1$-$C_6$ alkynyl, —$OR^9$, —$N(R^9)_2$, —(C═O)—$R^9$, —O—(C═O)—$R^9$, and —($NR^9$)—(C═O)—$R^9$;

each instance of $R^9$ is independently selected from the group consisting of H, $C_1$-$C_6$ alkyl, $C_1$-$C_6$ alkenyl, and $C_1$-$C_6$ alkynyl;

each instance of $R^1$, $R^2$, $R^3$, $R^4$, $R^5$, $R^6$, $R^7$, and $R^8$ is independently optionally substituted with one or more instances of $R^{10}$;

each instance of $R^{10}$ is independently selected from the group consisting of ═O, halogen, $C_1$-$C_4$ alkyl, $C_1$-$C_4$ alkenyl, $C_1$-$C_4$ alkynyl, —$OR^9$, —$N(R^9)_2$, —(C═O)—$R^9$, —O—(C═O)—$R^9$, and —($NR^9$)—(C═O)—$R^9$; and $X^1$ is $C(R^9)_2$, $NR^9$, O, or S.

In some cases, $R^1$ is H, $C_1$-$C_6$ alkyl, $C_1$-$C_6$ alkenyl, or $C_1$-$C_6$ alkynyl, $C_1$-$C_6$ cycloalkyl, or $C_1$-$C_6$ heterocycloalkyl. In some cases, $R^1$ is H, $C_1$-$C_6$ alkyl, $C_1$-$C_6$ alkenyl, or $C_1$-$C_6$ alkynyl. In some cases, $R^1$ is H, or $C_1$-$C_6$ alkyl. In some cases, $R^1$ is H, or $C_1$-$C_4$ alkyl. In some cases, $R^1$ is H or methyl. In some cases, $R^1$ is H. In some cases, $R^1$ is methyl. In some cases, $R^1$ is substituted with at least one instance of $R^{10}$. In some cases, $R^1$ is substituted with at least two instances of $R^{10}$. In some cases, $R^1$ and its substituents comprise no alkenyl groups. In some cases, $R^1$ and its substituents comprise no alkynyl groups. In some cases, $R^1$ and its substituents are inert under radical polymerization conditions. In some cases, $R^1$ comprises no instances of $R^{10}$ substitution.

In some cases, each instance of $R^2$, $R^3$, and $R^4$ is independently selected from the group consisting of $C_1$-$C_6$ alkyl, $C_1$-$C_6$ alkenyl, $C_1$-$C_6$ alkynyl, $C_1$-$C_6$ cycloalkyl, and $C_1$-$C_6$ heterocycloalkyl. In some cases, each instance of $R^2$, $R^3$, and $R^4$ is independently selected from the group consisting of $C_1$-$C_6$ alkyl, $C_1$-$C_6$ cycloalkyl, and $C_1$-$C_6$ heterocycloalkyl. In some cases, each instance of $R^2$, $R^3$, and $R^4$ is independently $C_1$-$C_6$ alkyl. In some cases, none of $R^2$, $R^3$, $R^4$, and their substituents comprise an alkenyl or an alkynyl. In some cases, none of $R^2$, $R^3$, $R^4$, and their substituents comprise an aromatic group. In some cases, $R^2$, $R^3$, $R^4$, and their constituents are inert under radical polymerization conditions. In some cases, $R^2$, $R^3$, and $R^4$ collectively comprise at least one instance of $R^{10}$ substitution. In some cases, $R^2$, $R^3$, and $R^4$ collectively comprise at least two instances of $R^{10}$ substitution. In some cases, $R^2$, $R^3$, and $R^4$ collectively comprise at least three instances of $R^{10}$ substitution. In some cases, $R^2$, $R^3$, and $R^4$ collectively comprise at most three instances of $R^{10}$ substitution. In some cases, $R^2$, $R^3$, and $R^4$ collectively comprise at most two instances of $R^{10}$ substitution. In some cases, $R^2$, $R^3$, and $R^4$ collectively comprise at most one instance of $R^{10}$ substitution. In some cases, $R^2$, $R^3$, and $R^4$ collectively comprise no instances of $R^{10}$ substitution.

In some cases, any two of $R^2$, $R^3$, and $R^4$ are taken together along with the carbon to which they are commonly attached to form $C_1$-$C_6$ cycloalkyl. In some cases, the cycloalkyl is a caged cycloalkyl. In some cases, the cycloalkyl is cyclobutyl, cyclopentyl, cyclohexyl, cycloheptyl, bicyclohexane, bicycloheptane, or bicyclooctane. In some cases, the cycloalkyl comprises at least one instance of $R^{10}$ substitution. In some cases, the cycloalkyl comprises at least two instances of $R^{10}$ substitution. In some cases, the cycloalkyl comprises at least three instances of $R^{10}$ substitution. In some cases, the cycloalkyl comprises at most three instances of $R^{10}$ substitution. In some cases, the cycloalkyl comprises at most two instances of $R^{10}$ substitution. In some cases, the cycloalkyl comprises at most one instance of $R^{10}$ substitution. In some cases, each instance of $R^{10}$ substitution on the cycloalkyl is $C_1$-$C_6$ alkyl. In some cases, each instance of $R^{10}$ substitution on the cycloalkyl is methyl. In some cases, the cycloalkyl comprises at no instances of $R^{10}$ substitution. In some cases, $R^2$ and $R^3$ are taken together along with the carbon to which they are commonly attached to form $C_1$-$C_6$ cycloalkyl, and $R^4$ is $C_1$-$C_4$ alkyl. In some cases, $R^2$ and $R^3$ are taken together along with the carbon to which they are commonly attached to form $C_1$-$C_6$ cycloalkyl, and $R^4$ is methyl.

In some cases, $R^2$, $R^3$, and $R^4$ are taken together along with the carbon to which they are commonly attached to form a caged ring. In some cases, the caged ring contains between 6 and 14 carbons. In some cases, the caged ring contains between 7 and 12 carbons. In some cases, the caged ring comprises bicyclohexane, bicycloheptane, or bicyclooctane. In some cases, the caged ring comprises bicyclo[3.1.1]heptane, bicyclo[2.2.1]heptane, or bicyclo[2.2.2]octane.

In some cases $R^2$, $R^3$, and $R^4$ are taken together along with the carbon to which they are commonly attached to form

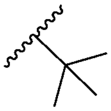 , 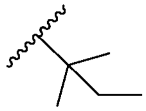 , 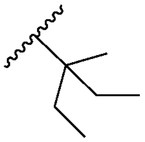 ,

-continued

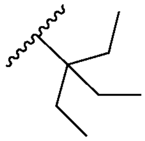 , 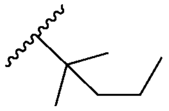 ,

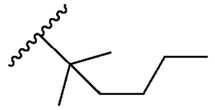 , 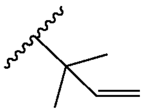 ,

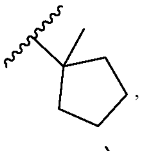 , 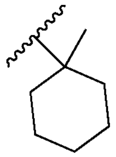 , 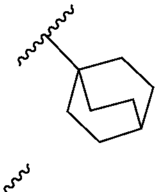 ,

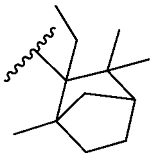 , or 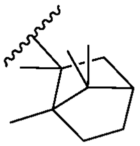 .

In some cases, $R^5$, $R^6$, $R^7$, and $R^8$ are each independently selected from the group consisting of H, $C_1$-$C_6$ alkyl, —$OR^9$, —$N(R^9)_2$, and —O—(C═O)—$R^9$. In some cases, $R^5$, $R^6$, $R^7$, and $R^8$ are each independently selected from the group consisting of H, $C_1$-$C_6$ alkyl, and —$OR^9$. In some cases, at least one of $R^5$, $R^6$, $R^7$, and $R^8$ is —$OR^9$. In some cases, at least two of $R^5$, $R^6$, $R^7$, and $R^8$ are —$OR^9$. In some cases, each of $R^5$, $R^6$, $R^7$, and $R^8$ is H or —$OR^9$. In some cases, at least one of $R^5$, $R^6$, $R^7$, and $R^8$ is H. In some cases, at least two of $R^5$, $R^6$, $R^7$, and $R^8$ are H. In some cases, $R^6$ and $R^7$ are H. In some cases, $R^5$ and $R^8$ are —$OR^9$. In some cases, $R^5$ and $R^8$ are —OMe.

In some cases, each instance of $R^9$ is independently selected from the group consisting of H and $C_1$-$C_6$ alkyl. In some cases, each instance of $R^9$ is independently selected from the group consisting of H and $C_1$-$C_4$ alkyl. In some cases, each instance of $R^9$ is independently selected from the group consisting of H and methyl. In some cases, no instance of $R^9$ comprises an alkenyl or alkynyl.

In some cases, each instance of $R^{10}$ is independently selected from the group consisting of ═O, $C_1$-$C_4$ alkyl, $C_1$-$C_4$ alkenyl, $C_1$-$C_4$ alkynyl, —$OR^9$, and —$N(R^9)_2$. In some cases, each instance of $R^{10}$ is independently selected from the group consisting of $C_1$-$C_4$ alkyl and —$OR^9$. In some cases, the polymerizable monomer comprises at least one instance of $R^{10}$. In some cases, the polymerizable monomer comprises at least two instances of $R^{10}$. In some cases, the polymerizable monomer comprises at most two instances of $R^{10}$. In some cases, the polymerizable monomer comprises at most one instance of $R^{10}$. In some cases, the polymerizable monomer comprises no instances of $R^{10}$.

In some cases, $X^1$ is $NR^9$ or O. In some cases, $X^1$ is $N(CH_3)$, NH, or O. In some cases, $X^1$ is O.

In some cases, the polymerizable monomer is monofunctional (e.g., comprises a single polymerizable group). As used herein, 'monofunctional' can denote that a species contains a single functional group configured to polymerize under a specific condition or in the presence of a particular catalyst. In certain cases, 'single polymerizable monomer' denotes that a species contains a single olefin or a single polymerizable olefin.

In some cases, the polymerizable monomer comprises a structure according to Formula (Ib):

(Ib)

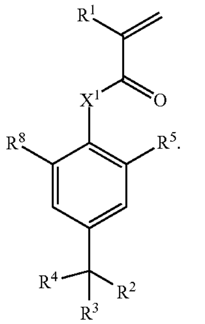

In some cases, neither of $R^5$ nor $R^8$ is H. In some cases, $R^5$ and $R^8$ are each —$OR^9$. In some cases, $R^5$ and $R^8$ are each —OMe.

Differing from some phenylacrylates, which can be liquid at room temperature and have high vapor pressures (for example syringyl acrylate and syringyl methacrylate, as outlined in TABLE 2), the polymerizable monomer of the present disclosure can have a low vapor pressure and a high boiling point. Such low vapor pressure can be particularly advantageous for use of such monomer in curable (e.g., photocurable) compositions and additive manufacturing where elevated temperatures (e.g., 60° C., 80° C., 90° C., or higher) may be used. In various instances, the polymerizable monomer can have a vapor pressure of at most about 0.1 Pascal (Pa), at most about 0.5 Pa, at most about 1 Pa, at most about 5 Pa, at most about 10 Pa, at most about 50 Pa, at most about 100 Pa, at most about 500 Pa, at most about 1 kilopascal (kPa), at most about 5 kPa, at most about 10 kPa, or at most about 50 kPa at 60° C. In various instances, the polymerizable monomer can have a vapor pressure of at most about 1 Pa to 5 Pa at 60° C. In various instances, the polymerizable monomer can have a vapor pressure of at most about 2 Pa to 5 Pa at 60° C. Thus, in some embodiments, the polymerizable monomer of the present disclosure can have a low mass loss at an elevated temperature. As used herein, a mass loss of a compound at a certain temperature (e.g., 90° C.) for a certain time period (e.g., 2 hours) can be used as a measure for volatility of such compounds. Herein, "substantially no volatility" can refer to a mass loss <1 wt % at the respective temperature (e.g., at 90° C. for 2 hours). In various instances, the polymerizable monomer of the present disclosure can have a mass loss <1 wt % at the respective temperature at 90° C. after heating at that temperature for 2 hours. In some embodiments, the polymerizable monomer can have a mass loss of less than about 0.5% after heating at 90° C. for 2 hours. In some embodiments, the polymerizable monomer can have a mass loss of about 0.1% to about 0.45% after heating at 90° C. for 2 hours. In some embodiments, the polymerizable monomer can have a mass loss of about 0.05% to about 0.25% after heating at 90° C. for 2 hours.

The polymerizable monomer can be liquid, solid, or crystalline at room temperature. In some cases, the polymerizable monomer is liquid or crystalline at room temperature. In some cases, the polymerizable monomer has a melting point of at least 50° C., at least 60° C., at least 70° C., at least 80° C., at least 90° C., at least 100° C., at least 110° C., at least 120° C., or at least 130° C. In some cases, the polymerizable monomer has a melting point of at least 70° C. In some cases, the polymerizable monomer has a melting point of at least 100° C. In some cases, the polymerizable monomer has a melting point of at most 130° C., at most 120° C., at most 110° C., at most 100° C., at most 90° C., at most 80° C., at most 70° C., at most 60° C., or at most 50° C. In some cases, the polymerizable monomer has a melting point of between about 70° C. and 130° C.

In some cases, the polymerizable monomer has a molecular weight of at least about 275 Da. In some cases, the polymerizable monomer has a molecular weight of at least about 300 Da. In some cases, the polymerizable monomer has a molecular weight of at least about 325 Da. In some cases, the polymerizable monomer has a molecular weight of at least about 350 Da. In some cases, the polymerizable monomer has a molecular weight of at least about 375 Da. In some cases, the polymerizable monomer has a molecular weight of at least about 400 Da. In some cases, the polymerizable monomer has a molecular weight of at most about 400 Da. In some cases, the polymerizable monomer has a molecular weight of at most about 375 Da. In some cases, the polymerizable monomer has a molecular weight of at most about 350 Da. In some cases, the polymerizable monomer has a molecular weight of at most about 325 Da. In some cases, the polymerizable monomer has a molecular weight of at most about 300 Da. In some cases, the polymerizable monomer has a molecular weight of between about 275 and 375 Da. In some cases, the polymerizable monomer has a molecular weight of between about 300 and 350 Da.

III. Polymerizable Monomer Synthesis

A polymerizable monomer may be generated through a two-step synthesis involving: (i) alkylating a phenol, a thiophenol, or an aniline, wherein the alkylating comprises coupling —$CR^2R^3R^4$ to the phenol, the thiophenol, or the aniline aryl; and (ii) coupling

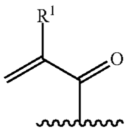

to the phenol hydroxyl, the aniline amine, or the thiophenol thiol to affect esterification, amidation, or thioesterification, respectively. An example of a such a method is provided in Scheme 1, in which HO—$C(R^2)(R^3)(R^4)$ is used for Friedel-Crafts alkylation, followed by phenol, thiophenol, or aniline alkylation using an acrylic or a methacrylic anhydride.

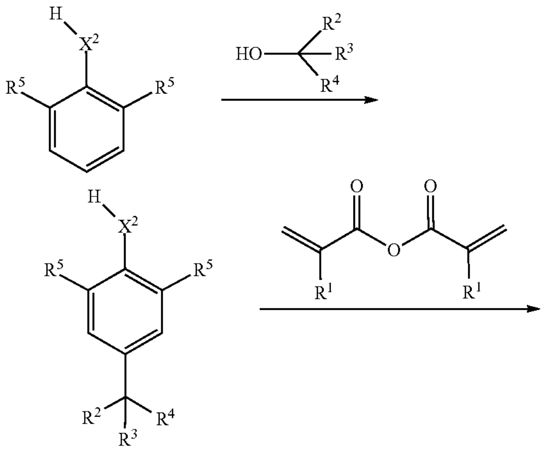

-continued

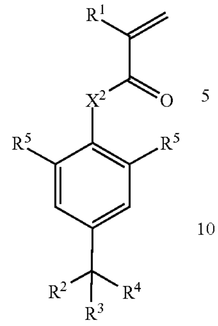

$X^2$ = O, S, or NH

In some cases, the polymerizable monomer is generated by coupling

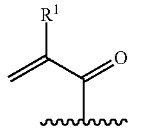

to a phenol hydroxyl, an aniline amine, or a thiophenol thiol. In some cases, the polymerizable monomer is generated by coupling —$CR^2R^3R^4$ to an acrylate, a thioacrylate, or an acrylamide aryl.

IV. Resin Components

A curable resin, such as a curable resin disclosed herein, can comprise one or more polymerizable species (e.g., a polymerizable monomer of Formula (I) or (Ib) and a telechelic oligomer) in an amount from about 5% by weight (w/w) to about 100% w/w. In some cases, the curable resin comprises from about 20% w/w to about 80% w/w, from about 30% w/w to about 75% w/w, from about 40% w/w to about 70% w/w, or from about 55% w/w to about 65% w/w polymerizable species.

A curable resin disclosed herein can comprise one or more species of polymerizable monomers (e.g., a compound of Formula (I) or (Ib)) in an amount from about 25% w/w to about 85% w/w, from about 35% w/w to about 70% w/w, from about 45% w/w to about 75% w/w, or from about 55% to 70% w/w. In some cases, a resin provided herein can comprise at least about 25%, at least about 30%, at least about 35%, at least about 40%, at least about 45%, at least about 50%, at least about 55%, at least about 60%, at least about 65%, at least about 70%, at least about 75%, at least about 80%, or at least about 85% w/w of the polymerizable monomer.

A curable resin can contain a low glass transition temperature (Tg) oligomer. The low Tg oligomer can have a molecular weight (e.g., weight average or number average molecular weight) of between about 400 and about 20000 Da. The low Tg oligomer can have a glass transition temperature of at most −30° C., at most −20° C., at most −10° C., at most 0° C., at most 10° C., at most 20° C., or at most 30° C.

In various embodiments, a curable resin herein is a photo-curable resin. Such photo-curable resin described herein can further comprise one or more photoinitiators. Such photoinitiator, when activated with light of an appropriate wavelength (e.g., UV/VIS) can initiate a polymerization reaction (e.g., during photo-curing) between the telechelic polymers, monomers, and other potentially polymerizable components that may be present in the photo-curable resin, to form a polymeric material as further described herein. Generally, photoinitiators described in the present disclosure can include those that can be activated with light and initiate polymerization of the polymerizable components of the formulation. A "photoinitiator", as used herein, may generally refer to a compound that can produce radical species and/or promote radical reactions upon exposure to radiation (e.g., UV or visible light).

In some embodiments, a photo-curable resin herein further comprises 0.05 to 1 wt %, 0.05 to 2 wt %, 0.05 to 3 wt %, 0.05 to 4 wt %, 0.05 to 5 wt %, 0.1 to 1 wt %, 0.1 to 2 wt %, 0.1 to 3 wt %, 0.2 to 1 wt %, 0.2 to 2 wt %, 0.2 to 3 wt %, 0.3 to 1 wt %, 0.3 to 2 wt %, 0.3 to 3 wt %, 0.4 to 1 wt %, 0.4 to 2 wt %, 0.4 to 3 wt %, 0.5 to 1 wt %, 0.5 to 2 wt %, or 0.5 to 3 wt % of a photoinitiator based on the total weight of the composition. In some embodiments, the photoinitiator is a free radical photoinitiator. In certain embodiments, the photoinitiator comprises a phosphine oxide, such as diphenyl(2,4,6-trimethylbenzoyl)phosphine oxide (TPO). In some cases, the photoinitiator comprises an alpha hydroxy ketone moiety (e.g., 2-hydroxy-2-methylpropiophenone or 1-hydroxycyclohexyl phenyl ketone), an alpha-amino ketone (e.g., 2-benzyl-2-(dimethylamino)-4'-morpholinobutyrophenone or 2-methyl-1-[4-(methylthio) phenyl]-2-morpholinopropan-1-one), 4-methyl benzophenone, an azo compound (e.g., 4,4'-Azobis(4-cyanovaleric acid), 1,1'-azobis(cyclohexanecarbonitrile, azobisisobutyronitrile, 2,2'-azobis(2-methylpropionitrile), or 2,2'-azobis(2-methylpropionitrile)), an inorganic peroxide, an organic peroxide, or any combination thereof. In some embodiments, the composition comprises a photoinitiator comprising SpeedCure TPO-L (ethyl phenyl(2,4,6-trimethylbenzoyl) phosphinate). In some embodiments, a photo-curable composition comprises a photoinitiator selected from a phosphine oxide, benzophenone, a mixture of benzophenone and a tertiary amine containing a carbonyl group which is directly bonded to at least one aromatic ring, and an Irgacure (e.g., Irgacure 907 (2-methyl-1-[4-(methylthio)-phenyl]-2-morpholino-propanone-1) or Irgacure 651 (2,2-dimethoxy-1,2-diphenylethan-1-one). In some embodiments, the photoinitiator comprises an acetophenone photoinitiator (e.g., 4'-hydroxyacetophenone, 4'0phenoxyacetophenone, 4'-ethoxyaceto-phenone), a benzoin, a benzoin derivative, a benzil, a benzil derivative, a benzophenone (e.g., 4-benzoylbiphenyl, 3,4-(dimethylamino) benzophenone, 2-methylbenzophenone), a cationic photoinitiator (e.g., diphenyliodonium nitrate, (4-iodophenyl)diphenylsulfonium triflate, triphenylsulfonium triflate), an anthraquinone, a quinone (e.g., camphorquinone), a phosphine oxide, a phosphinate, 9,10-phenanthrenequinone, a thioxanthone, any combination thereof, or any derivative thereof. In some cases, the photoinitiator comprises TPO.

In some embodiments, the photoinitiator can have a maximum wavelength absorbance between 200 and 300 nm, between 300 and 400 nm, between 400 and 500 nm, between 500 and 600 nm, between 600 and 700 nm, between 700 and 800 nm, between 800 and 900 nm, between 150 and 200 nm, between 200 and 250 nm, between 250 and 300 nm, between 300 and 350 nm, between 350 and 400 nm, between 400 and 450 nm, between 450 and 500 nm, between 500 and 550 nm, between 550 and 600 nm, between 600 and 650 nm, between 650 and 700 nm, or between 700 and 750 nm. In some embodiments, the photoinitiator has a maximum wavelength absorbance between 300 to 500 nm.

In some embodiments, a curable resin of the present disclosure comprises a crosslinker. As used herein, the term 'crosslinker' may denote a monomer, oligomer, or polymer which contains multiple reactive groups or sites which are capable of polymerizing. In many cases, the crosslinker may copolymerize with the polymerizable monomers of the present disclosure. For example, the crosslinker may comprise a plurality of olefins capable of coupling to an acrylate, methacrylate, acrylamide, methacrylamide, thioacrylate, or other reactive olefin of the polymerizable monomer. The crosslinker may be a monomer. The crosslinker may be an oligomer or a polymer. The crosslinker may comprise a molecular weight of about 200 to about 10000 Da, about 400 to about 8000 Da, about 500 to about 5000 Da, about 1000 to about 3000 Da, or about 1500 to about 2500 Da. A resin may comprise between about 1% and about 30% w/w of the crosslinker. A resin may comprise between about 2% and about 20% w/w of the crosslinker. A resin may comprise between about 4% and about 16% w/w of the crosslinker. A resin may comprise between about 6% and 11% w/w of the crosslinker.

In some embodiments, a curable resin of the present disclosure can further comprise a crosslinking modifier (e.g., in addition to a polymerizable monomer disclosed herein that can act as a cross-linker, or in instances where the polymerizable monomer does not act as a cross-linker), a light blocker, a solvent, a glass transition temperature modifier, or a combination thereof. In some aspects, the curable resin comprises 0-25 wt % of the crosslinking modifier, the crosslinking modifier having a number-average molecular weight equal to or less than 1,500 Da. In some aspects, the curable resin comprises from 0 to 10 wt %, from 0 to 9 wt %, from 0 to 8 wt %, from 0 to 7 wt %, from 0 to 6 wt %, from 0 to 5 wt %, from 0 to 4 wt %, from 0 to 3 wt %, from 0 to 2 wt %, from 0 to 1 wt %, or from 0 to 0.5 wt % of the light blocker.

In some embodiments, the curable resin comprises a solvent. In some embodiments, the solvent comprises a nonpolar solvent. In certain embodiments, the nonpolar solvent comprises pentane, cyclopentane, hexane, cyclohexane, benzene, toluene, 1,4-dioxane, chloroform, diethyl ether, dichloromethane, a derivative thereof, or a combination thereof. In some embodiments, the solvent comprises a polar aprotic solvent. In certain embodiments, the polar aprotic solvent comprises tetrahydrofuran, ethyl acetate, acetone, dimethylformamide, acetonitrile, dimethyl sulfoxide, propylene carbonate, a derivative thereof, or a combination thereof. In some embodiments, the solvent comprises a polar protic solvent. In certain embodiments, the polar protic solvent comprises formic acid, n-butanol, isopropyl alcohol, n-propanol, t-butanol, ethanol, methanol, acetic acid, water, a derivative thereof, or a combination thereof. In some embodiments, the curable resin comprises less than 90% of the solvent by weight.

A curable resin, such as a curable resin disclosed herein, can comprise one or more species of telechelic polymers, telechelic oligomers, or a combination thereof, in an amount from about 15% w/w to about 60% w/w, from about 35% w/w to about 55% w/w, from about 40% w/w to about 55% w/w, or from about 40% w/w to about 50% w/w.

In some embodiments, a resin component (e.g., a crosslinking modifier, a polymerization catalyst, a polymerization inhibitor, a glass transition temperature modifier, a light blocker, a plasticizer, a solvent, a surface energy modifier, a pigment, a dye, a filler, or a biologically significant chemical) is functionalized so that it can be incorporated into the polymeric material so that it cannot readily be extracted from the final cured material. In certain embodiments, the polymerization catalyst, polymerization inhibitor, light blocker, plasticizer, surface energy modifier, pigment, dye, and/or filler, are functionalized to facilitate their incorporation into the cured polymeric material.

In some embodiments, a resin herein comprises a component in addition to a polymerizable monomer described herein that can alter the glass transition temperature of the cured polymeric material. In such instances, a glass transition temperature modifier (also referred to herein as a $T_g$ modifier or a glass transition modifier) can be present in a curable composition from about 0 to 50 wt %, based on the total weight of the composition. Inclusion of the $T_g$ modifier can lead to a high heat deflection temperature, which can be improve the performance of a material at elevated temperatures. In some embodiments, the curable composition comprises 0 to 80 wt %, 0 to 75 wt %, 0 to 70 wt %, 0 to 65 wt %, 0 to 60 wt %, 0 to 55 wt %, 0 to 50 wt %, 1 to 50 wt %, 2 to 50 wt %, 3 to 50 wt %, 4 to 50 wt %, 5 to 50 wt %, 10 to 50 wt %, 15 to 50 wt %, 20 to 50 wt %, 25 to 50 wt %, 30 to 50 wt %, 35 to 50 wt %, 0 to 40 wt %, 1 to 40 wt %, 2 to 40 wt %, 3 to 40 wt %, 4 to 40 wt %, 5 to 40 wt %, 10 to 40 wt %, 15 to 40 wt %, or 20 to 40 wt % of a $T_g$ modifier. In certain embodiments, the curable composition comprises 0-50 wt % of a glass transition modifier. In some instances, the number average molecular weight of the $T_g$ modifier is 0.4 to 5 kDa. In some embodiments, the number average molecular weight of the $T_g$ modifier is from 0.1 to 5 kDa, from 0.2 to 5 kDa, from 0.3 to 5 kDa, from 0.4 to 5 kDa, from 0.5 to 5 kDa, from 0.6 to 5 kDa, from 0.7 to 5 kDa, from 0.8 to 5 kDa, from 0.9 to 5 kDa, from 1.0 to 5 kDa, from 0.1 to 4 kDa, from 0.2 to 4 kDa, from 0.3 to 4 kDa, from 0.4 to 4 kDa, from 0.5 to 4 kDa, from 0.6 to 4 kDa, from 0.7 to 4 kDa, from 0.8 to 4 kDa, from 0.9 to 4 kDa, from 1 to 4 kDa, from 0.1 to 3 kDa, from 0.2 to 3 kDa, from 0.3 to 3 kDa, from 0.4 to 3 kDa, from 0.5 to 3 kDa, from 0.6 to 3 kDa, from 0.7 to 3 kDa, from 0.8 to 3 kDa, from 0.9 to 3 kDa, or from 1 to 3 kDa. A polymerizable monomer of the present disclosure (which can, in some cases, act by itself as a $T_g$ modifier) and a separate $T_g$ modifier compound can be miscible and compatible in the methods described herein. When used in the subject compositions, the $T_g$ modifier may provide for high $T_g$ and strength values, sometimes at the expense of elongation at break. In some cases, a toughness modifier may provide for high elongation at break and toughness via strengthening effects, and a polymerizable monomer described herein may improve the processability of the formulations (e.g., by acting as a reactive diluent) particularly of those compositions comprising high amounts of toughness modifiers, while maintaining high values for strength and $T_g$.

V. Resin Properties

A curable (e.g., photo-curable) resin herein can be characterized by having one or more properties. In some embodiments, a photo-polymerizable monomer, e.g., a compound of Formula (I) or (Ib) can be used as a reactive diluent in curable resins disclosed herein. Hence, in some instances, a photo-polymerizable monomer can reduce a viscosity of the curable resin (e.g., a photo-curable resin). In such cases, a photo-polymerizable monomer can reduce the viscosity of the curable resin by at least about 5% compared to a resin that does not comprise the polymerizable monomer. In some instances, a photo-polymerizable monomer can reduce the viscosity of a curable resin by at least about 5%, 10%, 20%, 30%, 40%, or 50%. In some instances, a curable resin of this disclosure can have a viscosity from about 30 cP to about 50,000 cP at a printing temperature. In some embodiments, the curable resin has a viscosity less than or equal to 30,000 cP, less than or equal to 25,000 cP, less than or equal to 20,000 cP, less than or equal to 19,000 cP, less than or equal to 18,000 cP, less than or equal to 17,000 cP, less than or equal to 16,000 cP, less than or equal to 15,000 cP, less than or equal to 14,000 cP, less than or equal to 13,000 cP, less than or equal to 12,000 cP, less than or equal to 11,000 cP, less than or equal to 10,000 cP, less than or equal to 9,000 cP, less than or equal to 8,000 cP, less than or equal to 7,000 cP, less than or equal to 6,000 cP, or less than or equal to 5,000 cP at 25° C. In some embodiments, the resin has a viscosity less than 15,000 cP at 25° C. In some embodiments, the curable resin has a viscosity less than or equal to 100,000 cP, less than or equal to 90,000 cP, less than or equal to 80,000 cP, less than or equal to 70,000 cP, less than or equal to 60,000 cP, less than or equal to 50,000 cP, less than or equal to 40,000 cP, less than or equal to 35,000 cP, less than or equal to 30,000 cP, less than or equal to 25,000 cP, less than or equal to 20,000 cP, less than or equal to 15,000 cP, less than or equal to 10,000 cP, less than or equal to 5,000 cP, less than or equal to 4,000 cP, less than or equal to 3,000 cP, less than or equal to 2,000 cP, less than or equal to 1,000 cP, less than or equal to 750 cP, less than or equal to 500 cP, less than or equal to 250 cP, less than or equal to 100 cP, less than or equal to 90 cP, less than or equal to 80 cP, less than or equal to 70 cP, less than or equal to 60 cP, less than or equal to 50 cP, less than or equal to 40 cP, less than or equal to 30 cP, less than or equal to 20 cP, or less than or equal to 10 cP at a printing temperature. In some embodiments, the curable resin has a viscosity from 50,000 cP to 30 cP, from 40,000 cP to 30 cP, from 30,000 cP to 30 cP, from 20,000 cP to 30 cP, from 10,000 cP to 30 cP, or from 5,000 cP to 30 cP at a printing temperature. In some embodiments, the printing temperature is from 0° C. to 25° C., from 25° C. to 40° C., from 40° C. to 100° C., or from 20° C. to 150° C. In some embodiments, the curable resin has a viscosity from 30 cP to 50,000 cP at a printing temperature, wherein the printing temperature is from 20° C. to 150° C. In yet other embodiments, the curable resin has a viscosity less than 20,000 cP at a print temperature. In some embodiments, the print temperature is from 10° C. to 200° C., from 30° C. to 175° C., from 50° C. to 150° C., or from 75° C. to 125° C. In preferred embodiments, the print temperature is from 75° C. to 100° C.

A curable resin of the present disclosure can be capable of being 3D printed at a temperature greater than 25° C. In some cases, the printing temperature is at least about 30° C., 40° C., 50° C., 60° C., 80° C., or 100° C. As described herein, a photo-polymerizable monomer of this disclosure that can part of the curable resin, can have a low vapor pressure and/or mass loss at the printing temperature, thereby providing improved printing conditions compared to conventional resins used in additive manufacturing.

In some embodiments, a curable resin herein has a melting temperature greater than room temperature. In some embodiments, the curable resin has a melting temperature greater than 20° C., greater than 25° C., greater than 30° C., greater than 35° C., greater than 40° C., greater than 45° C. greater than 50° C., greater than 55° C., greater than 60° C., greater than 65° C., greater than 70° C., greater than 75° C., or greater than 80° C. In some embodiments, the curable resin has a melting temperature from 20° C. to 250° C., from 30° C. to 180° C., from 40° C. to 160° C., or from 50° C. to 140° C. In some embodiments, the curable resin has a melting temperature greater than 60° C. In other embodiments, the curable resin has a melting temperature from 80° C. to 110° C. In some instances, a curable resin can have a melting temperature of about 80° C. before polymerization, and after polymerization, the resulting polymeric material can have a melting temperature of about 100° C.

In certain instances, it may be advantageous that a curable resin is in a liquid phase at an elevated temperature. As an example, a conventional curable resin can comprise polymerizable components that may be viscous at a process temperature, and thus can be difficult to use in the fabrication of objects (e.g., using 3D printing). As a solution for that technical problem, the present disclosure provides curable resins comprising photo-polymerizable components such as monomers described herein that can melt at an elevated temperature, e.g., at a temperature of fabrication (e.g., during 3D printing), and can have a decreased viscosity at the elevated temperature, which can make such resin more applicable and usable for uses such as 3D printing. Hence, in some embodiments, provided herein are curable resins that are a liquid at an elevated temperature. In some embodiments, the elevated temperature is at or above the melting temperature (Tm) of the curable resin. In certain embodiments, the elevated temperature is a temperature in the range from about 40° C. to about 100° C., from about 60° C. to about 100° C., from about 80° C. to about 100° C., from about 40° C. to about 150° C., or from about 150° C. to about 350° C. In some embodiments, the elevated temperature is a temperature above about 40° C., above about 60° C., above about 80° C., or above about 100° C. In some embodiments, a curable resin herein is a liquid at an elevated temperature with a viscosity less than about 50 PaS, less than 2 about 0 PaS, less than about 10 PaS, less than about 5 PaS, or less than about 1 PaS. In some embodiments, a curable resin herein is a liquid at an elevated temperature of above about 40° C. with a viscosity less than about 20 PaS. In yet other embodiments, a curable resin herein is a liquid at an elevated temperature of above about 40° C. with a viscosity less than about 1 PaS.

In some embodiments, at least a portion of a curable resin herein has a melting temperature below about 100° C., below about 90° C., below about 80° C., below about 70° C., or below about 60° C. In some embodiments, at least a portion of a curable resin herein melts at an elevated temperature between about 100° C. and about 20° C., between about 90° C. and about 20° C., between about 80° C. and about 20° C., between about 70° C. and about 20° C., between about 60° C. and about 20° C., between about 60° C. and about 10° C., or between about 60° C. and about 0° C.

In various embodiments, a curable resin herein as well as its photo-polymerizable components can be biocompatible, bioinert, or a combination thereof. In various instances, the photo-polymerizable monomers of a resin herein can have biocompatible and/or bioinert metabolic (e.g., hydrolysis) products.

A curable resin of the present disclosure can comprise less than about 20 wt % or less than about 10 wt % hydrogen bonding units. In some aspects, a curable resin herein comprises less than about 15 wt %, less than about 10 wt %, less than about 9 wt %, less than about 8 wt %, less than about 7 wt %, less than about 6 wt %, less than about 5 wt %, less than about 4 wt %, less than about 3 wt %, less than about 2 wt %, or less than about 1 wt % hydrogen bonding units.

A curable resin of the present disclosure may be homogenous, or may comprise a degree of phase separation. A curable resin of the present disclosure may be an emulsion.

VI. Polymeric Materials

The present disclosure provides polymeric materials. Such polymeric materials can be generated by curing a curable composition or resin described herein. A polymeric material provided herein can be biocompatible, bioinert, or a combination thereof. In various instances, a polymeric material herein is generated by photo-curing a photo-curable composition described herein. Such photo-curable compositions can comprise one or more polymerizable monomers of the present disclosure, e.g., the polymerizable monomer of Formula (I) or (Ib).

As described herein, advantages of the polymerizable monomers of the present disclosure can include (i) lower amounts of reactive diluent that may be needed in a curable resin to provide polymeric materials with properties suitable for various medical devices, at least in part due to the ability of the polymerizable monomers to provide continuous, uniform polymer matrices with interpenetrating and/or pseudo-interpenetrating polymer network, and (ii) reduced leaching of components from a polymeric material. In an example, polymerizable monomeric compounds such as reactive diluent molecules can have the tendency to leach out of polymeric materials post-curing in conventional materials that do not utilize the polymerizable monomers of the present disclosure. To solve such problem, the present disclosure provides polymerizable monomers that can comprise a plurality of reactive functional groups at each terminus—compared to only a single reactive functional group per terminus in conventional resin components—thereby statistically increasing the chance that all polymerizable components present in a resin are polymerized and incorporated into the polymeric network. Hence, in some instances, at most about 1%, 0.75%, 0.5%, 0.25%, or 0.1% w/w of a polymerizable component that was present in a curable resin is released from a formed polymeric material. In some cases, such polymerizable component is a polymerizable monomer, such as a reactive diluent. In some instances, such polymerizable component is released from the polymeric material in its monomeric and/or unreacted form. The amount of polymerizable component(s) released by a polymeric material can be determined by storing the polymeric material for 24 hours in a wet environment at 37° C., and then analytically measure the amount of component(s) released from the material based on the amount of component present in the initial curable resin that was used to generate the polymeric material.

Phase Separation in Polymeric Materials

Figure 5:
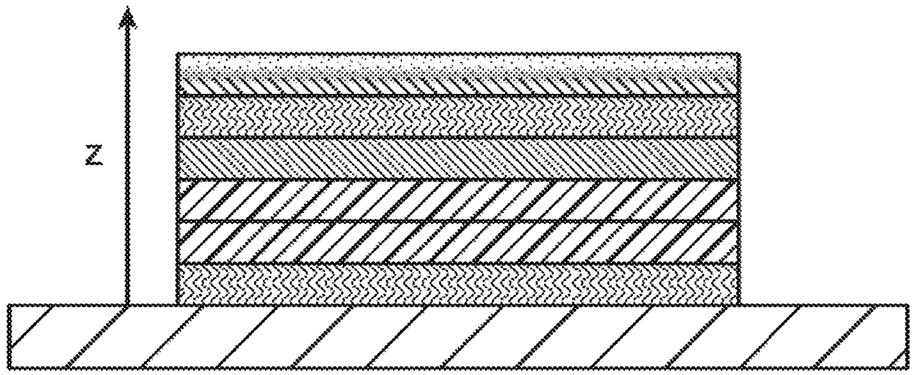
FIG. 5 illustrates the lateral dimensions and vertical dimension as used herein, e.g., in embodiments describing polymerization-induced phase separation.
Figure 5:
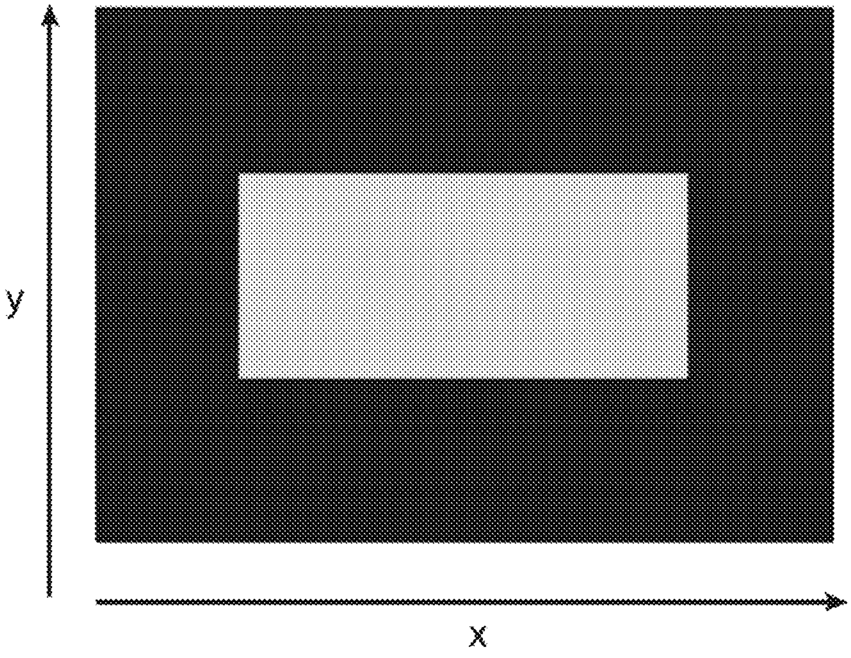

In some aspects herein, a curable composition or resin (e.g., a photo-curable resin) herein can be cured by exposing such composition or resin to electromagnetic radiation of appropriate wavelength. Such curing or polymerization can induce phase separation in the photo-curable composition and/or in the forming polymeric material. Such polymerization-induced phase separation can occur along one or more lateral and vertical direction(s) (see, e.g., FIG. 5). Polymerization-induced phase separation can generate one or more polymeric phases in the resulting polymeric material. A photo-curable composition undergoing polymerization and polymerization-induced phase separation can comprise one or more photo-polymerizable monomers of the present disclosure. Thus, in some cases, at least one polymeric phase of the one or more polymeric phases generated during curing and present in the resulting polymeric material can comprise, in a polymerized form, at least one of the one or more photo-polymerizable monomers. In an example, a photo-curable resin comprising one photo-polymerizable monomer species is cured by exposure to electromagnetic radiation of appropriate wavelength. The cured polymeric material comprises 2 polymeric phases A and B. In some cases, at least one of the phases A or B can comprise the photo-polymerizable monomer as a component in its polymeric structure. In some cases, both phases A and B can comprise the photo-polymerizable monomer as a component in their polymeric structure. The phases A and B can comprise the photo-polymerizable monomer in different amounts or concentrations. Thus, in some cases herein, two or more phase that comprise a photo-polymerizable monomer of this disclosure can be separated by a concentration gradient of such monomer.

A polymeric phase of a polymeric material of the present disclosure can have a certain size or volume. In some embodiments, a polymeric phase is 3-dimensional, and can have at least one dimension with less than 1000 μm, less than 500 μm, less than 250 μm, less than 200 μm, less than 150 μm, less than 100 μm, less than 90 μm, less than 80 μm, less than 70 μm, less than 60 μm, less than 50 μm, less than 40 μm, less than 30 μm, less than 20 μm, or less than 10 μm. In certain embodiments, the polymeric phase can have at least two dimensions with less than 1000 μm, less than 500 μm, less than 250 μm, less than 200 μm, less than 150 μm, less than 100 μm, less than 90 μm, less than 80 μm, less than 70 μm, less than 60 μm, less than 50 μm, less than 40 μm, less than 30 μm, less than 20 μm, or less than 10 μm. In certain embodiments, the polymeric phase can have three dimensions with less than 1000 μm, less than 500 μm, less than 250 μm, less than 200 μm, less than 150 μm, less than 100 μm, less than 90 μm, less than 80 μm, less than 70 μm, less than 60 μm, less than 50 μm, less than 40 μm, less than 30 μm, less than 20 μm, or less than 10 μm. In some aspects, a polymeric material comprises an average polymeric phase size of less than about 5 μm in at least one spatial dimension.

In various aspects, the present disclosure provides a polymeric material that can comprise one or more polymeric phases, wherein at least one polymeric phase of the one or more polymeric phases is a crystalline phase. In various aspects, the present disclosure provides a polymeric material that can comprise one or more polymeric phases, wherein at least one polymeric phase of the one or more polymeric phases is an amorphous phase. In some instances, provided herein is a polymeric material that can comprise two or more polymeric phases, wherein at least one polymeric phase of the one or more polymeric phases is a crystalline phase, and at least one polymeric phase of the one or more polymeric phases an amorphous phase.

Hence, in some instance, provided herein is a polymeric material comprising: (i) at least one crystalline phase comprising at least one polymer crystal having a melting temperature above 20° C.; and (ii) at least one amorphous phase comprising at least one amorphous polymer having a glass transition temperature greater than 40° C. In some cases, the at least one crystalline phase can comprise, in a polymerized form, a photo-polymerizable monomer according to Formula (I) or (Ib). In some cases, the at least one amorphous phase can comprise, in a polymerized form, a photo-polymerizable monomer according to Formula (I) or (Ib). In some aspects, such amorphous phase has a glass transition temperature greater than 50° C., 60° C., 70° C., 80° C., 90° C., 100° C. or greater than 110° C. In some instances, such amorphous phase can comprise, in a polymerized form, a polymerizable monomer of the present disclosure.

Amorphous Polymeric Phases

The present disclosure provides polymeric materials comprising one or more amorphous phases, e.g., generated by polymerization-induced phase separation. Such polymeric materials, or regions of such material that contain polymeric phases, can provide fast response times to external stimuli, which can confer favorable properties to the polymeric material comprising the crystalline phase and/or the amorphous phase, e.g., for using the polymeric material in a medical device (e.g., an orthodontic appliance). In some cases, a polymeric material comprising one or more amorphous polymeric phases can, for example, provide flexibility to the cured polymeric material, which can increase its durability (e.g., the material can be stretched or bent while retaining its structure, while a similar material without amorphous phases can crack). In certain embodiments, amorphous phases can be characterized by randomly oriented polymer chains (e.g., not stacked in parallel or in crystalline structures). In some embodiments, such amorphous polymeric phase of a polymeric material can have a glass transition temperature of greater than about 10° C., 20° C., 30° C., 40° C., 50° C., 60° C., 70° C., 80° C., 90° C., 100° C., or greater than about 110° C. In some embodiments, an amorphous polymeric phase can have a glass transition temperature from about 40° C. to about 60° C., from about 50° C. to about 70° C., from about 60° C. to about 80° C., or from about 80° C. to about 110° C.

In some embodiments, an amorphous phase herein (also referred to herein as an amorphous domain) can comprise at least about 5%, 10%, 20%, 30%, 40%, 50%, 60%, 70%, 80% or at least about 90% amorphous polymeric material in an amorphous state. The percentage of amorphous polymeric material in an amorphous phase generally refers to total volume percent.

In some embodiments, an amorphous polymeric phase can comprise one or more polymer types that may have formed, during curing, from the polymerizable monomers, telechelic polymers and/or oligomers, polymerizable monomers, and any other polymerizable component that may have been present in the curable composition used to produce the polymeric material that contains the amorphous polymeric phase. In some instances, such one or more polymer types can include one or more of comprises a homopolymer, a linear copolymer, a block copolymer, an alternating copolymer, a periodic copolymer, a statistical copolymer, a random copolymer, a gradient copolymer, a branched copolymer, a brush copolymer, a comb copolymer, a dendrimer, or any combination thereof. In some cases, the amorphous polymeric material comprises a random copolymer. In some embodiments, the amorphous polymeric material can comprise poly-(ethylene) glycol (PEG), poly (ethylene) glycol diacrylate, PEG-THF, polytetrahydrofuran, poly-(tert-butyl acrylate), poly(ethylene-co-maleic anhydride), any derivative thereof, or any combination thereof.

In some instances, polymerizable components of a resin that can form a crystalline material, can form an amorphous phase instead when exposed to conditions that prevent their crystallization. Hence, in some cases, materials that may conventionally be considered crystalline can be used as amorphous material. As a non-limiting example, polycaprolactone can be a crystalline polymer, but when mixed with other polymerizable monomers, monomers and telechelic polymers, crystal formation may be prevented and an amorphous phase can form.

An amorphous phase can comprise, in a polymerized form, and in addition to one or more polymerizable monomers according to Formula (I) or (Ib), one or more of the following moieties: an acrylic monomer, an acrylamide, a methacrylamide, an acrylonitrile, a bisphenol acrylic, a carbohydrate, a fluorinated acrylic, a maleimide, an acrylate, 4-acetoxyphenethyl acrylate, acryloyl chloride, 4-acryloylmorpholine, 2-(acryloyloxy)ethyl]-trimethylammonium chloride, 2-(4-benzoyl-3-hydroxyphenoxy)ethyl acrylate, benzyl 2-propylacrylate, butyl acrylate, tert-butyl acrylate, 2[(butylamino)carbonyl]-oxy]ethyl acrylate, tert-butyl 2-bromoacrylate, 2-carboxyethyl acrylate, 2-chloroethyl acrylate, 2-(diethylamino)-ethyl acrylate, di(ethylene glycol) ethyl ether acrylate, 2-(dimethylamino)ethyl acrylate, 3-(dimethylamino)propyl acrylate, dipentaerythriol penta-/hexa-acrylate, ethyl acrylate, 2-ethylacryloyl chloride, ethyl 2-(bromomethyl)acrylate, ethyl cis-(beta-cyano)acrylate, ethylene glycol dicyclopentenyl ether acrylate, ethylene glycol methyl ether acrylate, ethylene glycol phenyl ether acrylate, ethyl 2-ethylacrylate, 2-ethylexyl acrylate, ethyl 2-propylacrylate, ethyl 2-(trimethylsilylmethyl)acrylate, hexyl acrylate, 4-hydroxybutyl acrylate, 2-hydroxyethyl acrylate, 2-hydroxy-3-phenoxypropyl acrylate, hydroxypropyl acrylate, isobornyl acrylate, isobutyl acrylate, isodecyl acrylate, isooctyl acrylate, lauryl acrylate, methyl 2-acetamidoacrylate, methyl acrylate, a methylene malonate (e.g., dibutyl methylene malonate, dihexyl methylene malonate, or dicyclohexyl methylene malonate), a methylene malonate macromerer (e.g., a polyester of 2-methylenemalonate such as Forza B3000 XP), methyl α-bromoacrylate, methyl 2-(bromo-methyl)acrylate, methyl 2-(chloromethyl)acrylate, methyl 3-hydroxy-2-methylenebutyrate, methyl 2-(trifluoromethyl)acrylate, octadecyl acrylate, pentabromobenzyl acrylate, pentabromophenyl acrylate, pentafluorophenyl acrylate, poly(ethylene glycol) diacrylate, poly-(ethylene glycol) methyl ether acrylate, poly(propylene glycol) acrylate, epoxidized soybean oil acrylate, 3-sulfopropyl acrylate, tetrahydrofuryl acrylate, 2-tetrahydropyranyl acrylate, 3-(trimethoxysilyl)propyl acrylate, 3,5,5-trimethylhexyl acrylate, 10-undecenyl acrylate, urethane acrylate, urethane acrylate methacrylate, tricylcodecane diacrylate, isobornyl acrylate, a methacrylate, allyl methacrylate, benzyl methacrylate, (2-boc-amino)ethyl methacrylate, tert-butyl methacrylate, 9H-carbazole-9-ethylmethacrylate, 3-chloro-2-hydroxypropyl methacrylate, cyclohexyl methacrylate, 1,10-decamethylene glycol dimethacrylate, ethylene glycol dicyclopentenyl ether methacrylate, ethylene glycol methyl ether methacrylate, 2-ethylhexyl methacrylate, furfuryl methacrylate, glycidyl methacrylate, glycosyloxyethyl methacrylate, hexyl methacrylate, hydroxybutyl methacrylate, 2-hydroxy-5-N-methacrylamidobenzoic acid, isobutyl methacrylate, methacryloyl chloride, methyl methacrylate, mono-2-methacryloyloxy)ethyl succinate, 2-N-morpholinoethyl methacrylate, 1-naphthyl methacrylate, pentabromophenyl methacrylate, phenyl methacrylate, pentabromophenyl methacrylate, TEMPO methacrylate, 3-sulfopropyl methacrylate, triethylene glycol methyl ether methacrylate, 2-[(1',1',1'-trifluoro-2'-(trifluoromethyl)-2'Ohdroxy)propyl]-3-norbornyl methacrylate, 3,3,5-trimethylcyclohexyl methacrylate, (trimethylsilyl)methacrylate, vinyl methacrylate, isobornyl methacrylate, bisphenol A dimethacrylate, an Omnilane OC, tert-butyl acrylate, isodecyl acrylate, tricylcodecane diacrylate, a polyfunctional acrylate, N,N'-methylenebisacrylamide, 3-(acryloyloxy)-2-hydroxypropyl) methacrylate, bis[2-(methacryloyloxy)ethyl] phosphate, 1,3-butanediol diacrylate, 1,4-butanediol diacrylate, diurethane dimethacrylate, N,N'-ethylenebis(acrylamide), glycerol 1,3-diglycerolate diacrylate, 1,6-hexanediol diacrylate, hydroxypivalyl hydroxypivalate bis[6-(acryloyloxy)hexanoate], neopentyl glycol diacrylate, pentaerythritol diacrylate, 1,3,6-triacryloyl hexahydro-1,3,5-triazine, trimethlolpropane ethoxylate, tris[2-(acryloyloxy)ethyl] isocyanurate, any derivative thereof, or a combination thereof.

An amorphous phase of a polymeric material herein can comprise one or more reactive functional groups that can allow for further modification of the polymeric material, such as additional polymerization (e.g., post-curing). In some embodiments, an amorphous polymeric material comprises a plurality of reactive functional groups, and the reactive functional groups can be located at one or both terminal ends of the amorphous material, in-chain, at a pendant (e.g., a side group attached to the polymer backbone), or any combination thereof. Non-limiting examples of reactive functional groups include free radically polymerizable functionalities, photoactive groups, groups facilitating step growth polymerization, thermally reactive groups, and/or groups that facilitate bond formation (e.g., covalent bond formation). In some embodiments, the reactive functional groups comprise an acrylate, a methacrylate, an acrylamide, a vinyl group, a vinyl ether, a thiol, an allyl ether, a norbornene, a vinyl acetate, a maleate, a fumarate, a maleimide, an epoxide, a ring-strained cyclic ether, a ring-strained thioether, a cyclic ester, a cyclic carbonate, a cyclic silane, a cyclic siloxane, a hydroxyl, an amine, an isocyanate, a blocked isocyanate, an acid chloride, an activated ester, a Diels-Alder reactive group, a furan, a cyclopentadiene, an anhydride, a group favorable toward photodimerization (e.g., an anthracene, an acenaphthalene, or a coumarin), a group that photodegrades into a reactive species (e.g., Norrish Type 1 and 2 materials), an azide, a derivative thereof, or a combination thereof.

Crystalline Polymeric Phases

As further described herein, a polymeric material of the present disclosure can comprise one or more crystalline phases, e.g., generated by polymerization-induced phase separation during curing. As described herein, a crystalline phase is a polymeric phase of a cured polymeric material that comprises at least one polymer crystal. As disclosed herein, a crystalline phase may consist of a single polymeric crystal, or may comprise a plurality of polymeric crystals (e.g., a plurality of microcrystals).

In some embodiments, a crystalline polymeric phase can have a melting temperature equal to or greater than about 20° C., 30° C., 40° C., 50° C., 60° C., 70° C., 80° C., 90° C., 100° C., 120° C., or equal to or greater than about 150° C. In some cases, at least two crystalline phases of a plurality of crystalline phases can have a different melting temperature due to, e.g., differences in crystalline phase sizes, impurities, degree of cross-linking, chain lengths, thermal history, rates at which polymerization occurred, degree of phase separation, or any combination thereof. In some aspects, at least two crystalline phases of a polymeric material can each have a polymer crystal melting temperature within about 5° C. of each other. In some instances, such melting temperature difference can be less than about 5° C. In other instances, such melting temperature difference can be greater than about 5° C. In some aspects, each of the polymer crystal melting temperatures of a polymeric material can be from about 40° C. to about 100° C. In some aspects, at least about 80% of the crystalline domains of a polymeric material can comprise a polymer crystal having a melting temperature between about 40° C. and about 100° C.

In some embodiments, at least 80% of the crystalline phases have a crystal melting point at a temperature between 0° C. and 100° C. In some embodiments, at least 80% of the crystalline phases have a crystal melting point at a temperature between 40° C. and 60° C., between 40° C. and 80° C., between 40° C. and 100° C., between 60° C. and 80° C., between 60° C. and 100° C., between 80° C. and 100° C., or greater than 100° C. In some embodiments, at least 90% of the crystalline phases have a crystal melting point at a temperature between 0° C. and 100° C. In some embodiments, at least 90% of the crystalline phases have a crystal melting point at a temperature between 40° C. and 60° C., between 40° C. and 80° C., between 40° C. and 100° C., between 60° C. and 80° C., between 60° C. and 100° C., between 80° C. and 100° C., or greater than 100° C. In some embodiments, at least 95% of the crystalline phases have a crystal melting point at a temperature between 0° C. and 100° C. In some embodiments, at least 95% of the crystalline phases have a crystal melting point at a temperature between 40° C. and 60° C., between 40° C. and 80° C., between 40° C. and 100° C., between 60° C. and 80° C., between 60° C. and 100° C., between 80° C. and 100° C., or greater than 100° C.

In certain embodiments, the temperature at which a crystalline phase of a cured polymeric material melts can be controlled, e.g., by using different amounts and types of polymerizable components in the curable resin, e.g., different amounts and types of polymerizable monomers and polymerizable monomers described herein, different amounts and types of polymerizable monomers, telechelic polymer(s) and/or oligomer(s), and/or by using blocks of polymers (i.e., in copolymers) that have different crystal melting points.

In some embodiments, the curing of a resin can occur at an elevated temperature (e.g., at about 90° C.), and as the cured polymeric material cools to room temperature (e.g., 25° C.), the cooling can trigger the formation and/or growth of polymeric crystals in the polymeric material. In some instances, a polymeric material can be a solid at room temperature and can be crystalline-free, but can form crystalline phase over time. In such cases, a crystalline phase can form within 1 hour, within 2 hours, within 4 hours, within 8 hours, within 12 hours, within 18 hours, within 1 day, within 2 days, within 3 days, within 4 days, within 5 days, within 6 days, or within 7 days after cooling. In some embodiments, a crystalline phase can form while the cured polymeric material is in a cooled environment, e.g., an environment having a temperature from about 40° C. to about 30° C., from about 30° C. to about 20° C., from about 20° C. to about 10° C., from about 10° C. to about 0° C., from about 0° C. to about −10° C., from about −10° C. to about −20° C., from about −20° C. to about −30° C., or below about −30° C. In some instances, a polymeric material can be heated to an elevated temperature in order to induce crystallization or formation of crystalline phases. As a non-limiting example, a polymeric material that is near its glass transition temperature can comprise polymer chains that may not be mobile enough to organize into crystals, and thus further heating the material can increase chain mobility and induce formation of crystals.

In some embodiments, the generation, formation, and/or growth of a polymeric phase is spontaneous. In some embodiments, the generation, formation, and/or growth of a polymer crystal is facilitated by a trigger. In some embodiments, the trigger comprises the addition of a seeding particle (also referred to herein as a "seed"), which can induce crystallization. Such seeds can include, for example, finely ground solid material that has at least some properties similar to the forming crystals. In some embodiments, the trigger comprises a reduction of temperature. In certain embodiments, the reduction of temperature can include cooling the cured material to a temperature from 40° C. to 30° C., from 30° C. to 20° C., from 20° C. to 10° C., from 10° C. to 0° C., from 0° C. to −10° C., from −10° C. to −20° C., from −20° C. to −30° C., or below −30° C. In some embodiments, the trigger can comprise an increase in temperature. In certain embodiments, the increase of temperature can include heating the polymeric cured material to a temperature from 20° C. to 40° C., from 40° C. to 60° C., from 60° C. to 80° C., from 80° C. to 100° C., or above 100° C. In some embodiments, the trigger comprises a force placed on the cured polymeric material. In certain embodiments, the force includes squeezing, compacting, pulling, twisting, or providing any other physical force to the material. In some embodiments, the trigger comprises an electrical charge and/or electrical field applied to the material. In some embodiments, formation of one or more crystalline phases may be induced by more than one trigger (i.e., more than one type of trigger can facilitate the generation, formation, and/or growth of crystals). In some embodiments, the polymeric material comprises a plurality of crystalline phases, and at least two of the crystalline phase may be induced by different triggers.

In some embodiments, a polymeric material herein comprises a crystalline phase that has discontinuous phase transitions (e.g., first-order phase transitions). In some cases, a polymeric material has discontinuous phase transitions, due at least in part to the presence of one or more crystalline domains. As a non-limiting example, a cured polymeric material comprising one or more crystalline domains can, when heated to an elevated temperature, have one or more portions that melt at such elevated temperature, as well as one or more portions that remain solid.

In some embodiments, a cured polymeric material comprises crystalline phases that are continuous and/or discontinuous phases. A continuous phase can be a phase that can be traced or is connected from one side of a polymeric material to another side of the material; for instance, a closed-cell foam has material comprising the foam that can be traced across the sample, whereas the closed cells (bubbles) represent a discontinuous phase of air pockets. In some embodiments, the at least one crystalline phase forms a continuous phase while the at least one amorphous phase is discontinuous across the material. In another embodiment, the at least one crystalline phase is discontinuous and the at least one amorphous phase is continuous across the material. In another embodiment, both the at least one crystalline and the at least one amorphous phases are continuous across the material. In some embodiments, a polymeric material comprises a plurality of crystalline phases, wherein one or more crystalline phases of the plurality of crystalline phases have a high melting point (e.g., at least about 50° C., 70° C., or 90° C.) and are in a discontinuous phase, while another one or more crystalline phases of the plurality of crystalline phases have a low melting point (e.g., at less than about 50° C., 70° C., or 90° C.) and are in a continuous phase.

In some aspects, a polymeric material comprises an average crystalline phase size of less than about 100 μm, 50 μm, 20 μm, 10 μm, or less then about 5 μm in at least one spatial dimension.

In some aspects, a polymer crystal of a crystalline phase can comprise greater than about 40 wt %, greater than about 50 wt %, greater than about 60 wt %, greater than about 70 wt %, greater than about 80 wt %, or greater than about 90 wt % of linear polymers and/or linear oligomers.

In some aspects, a polymeric material described herein can have a crystalline phase content from about 10% to about 90%, from about 20% to about 80%, from about 30% to about 70%, from about 40% to about 95%, or from about 50% to about 95%, as measured by X-ray diffraction. In some aspects, a polymeric material herein can comprise a weight ratio of crystalline phases to amorphous phases from about 1:99 to about 99:1.

In various aspects, the present disclosure provides a polymeric material comprising: an amorphous phase; and a crystalline phase comprising a polymer having a tactic property. In some aspects, the tactic property comprises being isotactic, being syndiotactic, having a plurality of meso diads, having a plurality of racemo diads, having a plurality of isotactic triads, having a plurality of syndiotactic triads, or having a plurality of heterotactic triads. In some aspects, the polymeric material comprising the crystalline phase comprising the polymer having the tactic property has increased crystallinity compared to a comparable polymeric material comprising a comparable atactic polymer. In some aspects, greater than 50%, greater than 60%, greater than 70%, greater than 80%, greater than 90%, greater than 95%, or greater than 99% of the crystalline phase comprises the tactic property. In some aspects, greater than 50%, greater than 60%, greater than 70%, greater than 80%, greater than 90%, greater than 95%, or greater than 99% of the polymeric material comprises the tactic property. In some aspects, the polymeric material comprising the polymer having the tactic property is characterized by at least one of: an elongation at break greater than or equal to 5%; a storage modulus greater than or equal to 500 MPa; a tensile modulus greater than or equal to 500 MPa; and a stress remaining greater than or equal to 0.01 MPa. In some aspects, a comparable polymeric material comprising an atactic polymer comparable to the polymer having the tactic property is characterized by at least one of: an elongation at break less than 5%; a storage modulus less than 500 MPa; a tensile modulus less than 500 MPa; and a stress remaining less than 0.01 MPa. In some aspects, the polymeric material is at least partially crosslinked. In some aspects, the polymeric material is a thermoset or a thermoplastic. In some aspects, the polymeric material comprises semi-crystalline segments.

In some embodiments, a cured polymer such as a crosslinked polymer, can be characterized by a tensile stress-strain curve that displays a yield point after which the test specimen continues to elongate, but there is no (detectable) or only a very low increase in stress. Such yield point behavior typically occurs "near" the glass transition temperature, where the material is between the glassy and rubbery regimes and may be characterized as having viscoelastic behavior. In some embodiments, viscoelastic behavior is observed in the temperature range from about 20° C. to about 40° C. The yield stress is determined at the yield point. In some embodiments, the modulus is determined from the initial slope of the stress-strain curve or as the secant modulus at 1% strain (e.g. when there is no linear portion of the stress-strain curve). The elongation at yield is determined from the strain at the yield point. When the yield point occurs at a maximum in the stress, the ultimate tensile strength is less than the yield strength. For a tensile test specimen, the strain is defined by ln ($l/l_0$), which may be approximated by $(l-l_0)/l_0$ at small strains (e.g. less than approximately 10%) and the elongation is $l/l_0$, where l is the gauge length after some deformation has occurred and $l_0$ is the initial gauge length. The mechanical properties can depend on the temperature at which they are measured. The test temperature may be below the expected use temperature for a dental appliance such as 35° C. to 40° C. In embodiments, the test temperature is 23±2° C.

As provided further herein, the polymeric material comprising a crystalline phase (can also referred to herein as a crystalline domain) and an amorphous phase (can also referred to herein as an amorphous domain) can have improved characteristics, such as the ability to act quickly (e.g., vibrate quickly and react upon application of strain, from the elastic characteristics of the amorphous domain) and also provide strong modulus (e.g., are stiff and provide strength, from the crystalline domain). The polymer crystals disclosed herein can comprise closely stacked and/or packed polymer chains. In some embodiments, the polymer crystals comprise long oligomer or long polymer chains that are stacked in an organized fashion, overlapping in parallel. The polymer crystals can in some cases be pulled out of a crystalline phase, resulting in an elongation as the polymer chains of the polymer crystal are pulled (e.g., application of a force can pull the long polymer chain of the polymer crystal, thus introducing disorder to the stacked chains, pulling at least a portion out of its crystalline state without breaking the polymer chain). This is in contrast with fillers that are traditionally used in the formation of resins for materials with high flexural modulus, which can simply slip through the amorphous phase as forces are applied to the polymeric material or when the fillers are covalently bonded to the polymers causing a reduction in the elongation to break for the material. The use of polymer crystals in the resulting polymeric material can thus provide a less brittle product that can retain more of the original physical properties following use (i.e., are more durable), and retains elastic characteristics through the combination of amorphous and crystalline phases.

In some embodiments, a polymeric material herein comprises a ratio of crystalline polymeric phases to amorphous polymeric phases (wt/wt) of greater than about 1:10, greater than about 1:9, greater than about 1:8, greater than about 1:7, greater than about 1:6, greater than about 1:5, greater than about 1:4, greater than about 1:3, greater than about 1:2, greater than about 1:1, greater than about 2:1, greater than about 3:1, greater than about 4:1, greater than about 5:1, greater than about 6:1, greater than about 7:1, greater than about 8:1, greater than about 9:1, greater than about 10:1, greater than about 20:1, greater than about 30:1, greater than about 40:1, greater than about 50:1, or greater than about 99:1. In some embodiments, the polymeric material comprises a ratio of the crystallizable polymeric material to the amorphous polymeric material (wt/wt) of at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, or at least 99:1. In certain embodiments, the polymeric material comprises a ratio of crystalline polymeric phases to amorphous polymeric phases (wt/wt) of between 1:9 and 99:1, between 1:9 and 9:1, between 1:4 and 4:1, between 1:4 and 1:1, between 3:5 and 1:1, between 1:1 and 5:3, or between 1:1 and 4:1.

In some embodiments, a polymeric material of this disclosure comprises a ratio of crystalline polymeric phases to amorphous polymeric phases (vol/vol) of greater than about 1:10, greater than about 1:9, greater than about 1:8, greater than about 1:7, greater than about 1:6, greater than about 1:5, greater than about 1:4, greater than about 1:3, greater than about 1:2, greater than about 1:1, greater than about 2:1, greater than about 3:1, greater than about 4:1, greater than about 5:1, greater than about 6:1, greater than about 7:1, greater than about 8:1, greater than about 9:1, greater than about 10:1, greater than about 20:1, greater than about 30:1, greater than about 40:1, greater than about 50:1, or greater than about 99:1. In some embodiments, the polymeric material comprises a ratio of crystalline polymeric phases to amorphous polymeric phases (vol/vol) of at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, or at least 99:1. In certain embodiments, the polymeric material comprises a ratio of crystalline polymeric phases to amorphous polymeric phases (vol/vol) of between 1:9 and 99:1, between 1:9 and 9:1, between 1:4 and 4:1, between 1:4 and 1:1, between 3:5 and 1:1, between 1:1 and 5:3, or between 1:1 and 4:1.

Properties of Polymeric Materials

A polymeric material of this disclosure formed from the polymerization of a curable resin disclosed herein can provide advantageous characteristics compared to conventional polymeric materials. In some instances, and as described herein, a polymeric material can contain some percentage of crystallinity, which can impart an increased toughness and high modulus to the polymeric material, while in some circumstances being a 3D printable material. Furthermore, a polymeric material herein can further comprise one or more amorphous phases that can provide increased durability, prevention of crack formation, as well as the prevention of crack propagation. In some instances, a polymeric material can also have low amounts of water uptake, and can be solvent resistant. In some cases, a polymeric material can be characterized by one or more of the properties selected from the group consisting of elongation at break, storage modulus, tensile modulus, stress remaining, glass transition temperature, water uptake, hardness, color, transparency, hydrophobicity, lubricity, surface texture, percent crystallinity, phase composition ratio, phase domain size, and phase domain size and morphology. Further, as described herein, the polymeric materials provided herein can be used for a multitude of applications, including 3D printing, to form materials having favorable properties of both elasticity and stiffness. Specifically, a polymeric material of this disclosure can provide excellent flexural modulus, elastic modulus, elongation at break, or a combination thereof.

In various embodiments, a polymeric material herein can comprise or consist of a high toughness, e.g., through a tough polymer matrix, and the difference (or delta) between the elastic modulus measured at different strain rates (e.g., at 1.7 mm/min and 510 mm/min) can be low, e.g., lower than 80%, 70%, 60%, 50%, 40%, or lower than 30%, which can be an indication for a polymeric phase separation within the material.

In some embodiments, a polymeric material of the present disclosure can have one or more of the following characteristics: (A) a flexural modulus greater than or equal to 50 MPa, 100 MPa, or 200 MPa; (B) an elastic modulus of greater than or equal to 150 MPa, 250 MPa, 350 MPa, 450 MPa, 550 MPa, or between about 500 and 1000 MPa, or from about 550 to about 800 MPa C) an elongation at break greater than or equal to 5% before and after 24 hours in a wet environment at 37° C.; (D) a water uptake of less than 25 wt % when measured after 24 hours in a wet environment at 37° C.; (E) transmission of at least 30% of visible light through the polymeric material after 24 hours in a wet environment at 37° C.; and (F) comprises a plurality of polymeric phases, wherein at least one polymeric phase of the one or more polymeric phases has a Tg of at least 60° C., 80° C., 90° C., 100° C., or at least 110° C. In some instances, a polymeric material herein has at least two, three, four, five, or all characteristics of (A), (B), (C), (D), (E) and (F).

In some instances, the polymeric material can be characterized by a storage modulus of 0.1 MPa to 4000 MPa, a storage modulus of 300 MPa to 3000 MPa, or a storage modulus of 750 MPa to 3000 MPa after 24 hours in a wet environment at 37° C.

In some instances, the polymeric material herein can have a flexural stress remaining of 400 MPa or more, 300 MPa or more, 200 MPa or more, 180 MPa or more, 160 MPa or more, 120 MPa or more, 100 MPa or more, 80 MPa or more, 70 MPa or more, 60 MPa or more, after 24 hours in a wet environment at 37° C.

In some instances, the polymeric material can be characterized by an elongation at break greater than 10%, an elongation at break greater than 20%, an elongation at break greater than 30%, an elongation at break of 5% to 250%, an elongation at break of 20% to 250%, or an elongation at break value between 40% and 250% before and after 24 hours in a wet environment at 37° C.

A polymeric material can be characterized by a water uptake of less than 20 wt %, less than 15 wt %, less than 10 wt %, less than 5 wt %, less than 4 wt %, less than 3 wt %, less than 2 wt %, less than 1 wt %, less than 0.5 wt %, less than 0.25 wt %, or less than 0.1 wt % when measured after 24 hours in a wet environment at 37° C. In some cases, a polymeric material can have greater than 50%, 60%, or 70% conversion of double bonds to single bonds compared to the curable resin, as measured by FTIR.

In some instances, a polymeric material can have an ultimate tensile strength from 10 MPa to 100 MPa, from 15 MPa to 80 MPa, from 20 MPa to 60 MPa, from 10 MPa to 50 MPa, from 10 MPa to 45 MPa, from 25 MPa to 40 MPa, from 30 MPa to 45 MPa, or from 30 MPa to 40 MPa after 24 hours in a wet environment at 37° C.

In some instances, a polymeric material can have a low amount of hydrogen bonding which can facilitate a decreased uptake of water in comparison with conventional polymeric materials having greater amounts of hydrogen bonding. Thus, in some instances, a polymeric material herein can comprise less than about 10 wt %, less than about 9 wt %, less than about 8 wt %, less than about 7 wt %, less than about 6 wt %, less than about 5 wt %, less than about 4 wt %, less than about 3 wt %, less than about 2 wt %, less than about 1 wt %, or less than about 0.5 wt % water when fully saturated at use temperature (e.g., about 20° C., 25° C., 30° C., or 35° C.). In some instances, the use temperature can include the temperature of a human mouth (e.g., approximately 35-40° C.). The use temperature can be a temperature selected from −100-250° C., 0-90° C., 0-80° C., 0-70° C., 0-60° C., 0-50° C., 0-40° C., 0-30° C., 0-20° C., 0-10° C., 20-90° C., 20-80° C., 20-70° C., 20-60° C., 20-50° C., 20-40° C., 20-30° C., or below 0° C.

In some embodiments, a polymeric material herein comprises at least one crystalline phase and at least one amorphous phase, wherein the at least one crystalline phase, the at least one amorphous phase, or both, contain a polymerizable monomer and/or monomer of the present disclosure, which can be a compound according to Formula (I) or (Ib). In some instance, a combination of these two types of phases or domains can create a polymeric material that has a high modulus phase (e.g., the crystalline polymeric material can provide a high modulus) and a low modulus phase (e.g., provided by the presence of the amorphous polymeric material). By having these two phases, the polymeric material can have a high modulus and a high elongation, as well as high stress remaining following stress relaxation.

In various instances, the one or more amorphous phases of the polymeric material can have a glass transition temperature of at least about 30° C., 40° C., 50° C., 60° C., 70° C., 80° C., 90° C., 100° C., or at least about 110° C. In such cases, at least one amorphous phase of the one or more amorphous phases having a glass transition temperature of at least about 50° C. comprises, integrated in its polymeric structure, a polymerizable monomer of the present disclosure such as a compound according to Formula (I) or (Ib).

In some cases, a polymeric material can comprise a polymer crystal attached to the amorphous polymer. As non-limiting examples, the polymer crystal can be covalently bonded to, entangled with, cross-linked to, and/or otherwise associated with (e.g., through hydrophobic interactions, pi-stacking, or hydrogen bonding interactions) the amorphous polymeric material.

In some embodiments, a polymeric material herein can comprise crystalline and/or amorphous phases having a smaller size (e.g., less than about 5 μm). Smaller polymeric phases in a polymeric material can facilitate light passage and provide a polymeric material that appears clear. In contrast, larger polymeric phases (e.g., those larger than about 10 μm) can scatter light, for example when the refractive index of the polymer crystal is different from the refractive index of the amorphous phase adjacent to the polymer crystal (e.g., the amorphous material). In some cases, at least 40%, 50%, 60%, or 70% of visible light passes through the polymeric material after 24 hours in a wet environment at 37° C.

Thus, in some cases, it may be advantageous to have a polymeric material that comprises small polymeric phases such as crystalline or amorphous phases, e.g., as measured by the longest length of the phases. In some embodiments, such polymeric material comprises an average polymeric phase size that is less than 5 μm. In some cases, the maximum polymeric phase size of the polymeric materials can be about 5 μm. In some embodiments, at least about 50%, at least about 60%, at least about 70%, at least about 80%, at least about 90%, at least about 95%, or at least about 99% of the polymeric phases of the polymeric material have a size of less than about 5 μm. In yet other embodiments, a polymeric material comprises an average polymeric phase size that is less than about 1 μm. In some embodiments, the maximum polymer polymeric phase size of the cured polymeric materials is 1 μm. In some embodiments, at least about 50%, at least about 60%, at least about 70%, at least about 80%, at least about 90%, at least about 95%, or at least about 99% of the polymeric phases of the polymeric material have a size less than about 1 μm. In yet other embodiments, the polymeric material comprises an average polymeric phase size that is less than about 500 nm. In some embodiments, the maximum polymeric phase size of the cured polymeric materials is about 500 nm. In some embodiments, at least about 50%, at least about 60%, at least about 70%, at least about 80%, at least about 90%, at least about 95%, or at least about 99% of the polymeric phases of the polymeric material have a size less than 500 nm.

In some embodiments, the size of at least one or more of the polymeric phases (e.g., crystalline phases and amorphous phases) of a polymeric material can be controlled. Non-limiting examples of ways in which the size of the polymeric phases can be controlled includes: rapidly cooling the cured polymeric material, annealing the cured polymeric material at an elevated temperature (i.e., above room temperature), annealing the cured polymeric material at a temperature below room temperature, controlling the rate of polymerization, controlling the intensity of light during the curing step using light, controlling and/or adjusting polymerization temperature, exposing the cured polymeric material to sonic vibrations, and/or controlling the presence and amounts of impurities, and in particular for crystalline phases, adding crystallization-inducing chemicals or particles (e.g., crystallization seeds).

In some embodiments, the refractive index of the one or more crystalline phases and/or one or more amorphous phases of a polymeric material herein can be controlled. A reduction in difference of refractive index between different phases (e.g., reduction in the difference of refractive index between the crystalline polymer and the amorphous polymer) can increase clarity of the cured polymeric material, providing a clear or nearly clear material. Light scatter can be decreased by minimizing polymer crystal size, as well as by reducing the difference of refractive index across an interface between an amorphous polymeric phase and a crystalline phase. In some embodiments, the difference of refractive index between a given polymeric phase and a neighboring phase (e.g., crystalline and a neighboring amorphous phase) can be less than about 0.1, less than about 0.01, or less than about 0.001.

Further provided herein are polymeric films comprising a polymeric material of the present disclosure. In some cases, such polymeric film can have a thickness of at least about 50 m, 100 m, 250 m, 500 m, 1 mm, 2 mm and not more than 3 mm.

Polymeric Materials in Medical Devices

The present disclosure provides devices that comprise a polymeric material of the present disclosure. As described herein, such polymeric material can comprise, incorporated in its polymeric structure, one or more species of polymerizable monomer(s) of this disclosure, e.g., compounds according to Formula (I) or (Ib). In various cases, the device can be a medical device. The medical device can be an orthodontic appliance. The orthodontic appliance can be a dental aligner, a dental expander or a dental spacer.

VII. Methods of Use

The present disclosure provides methods for synthesizing the polymerizable monomer of the present disclosure, methods of using compositions (e.g., resins and polymeric materials) comprising such compounds, as well as methods for using the compositions in devices such as medical devices. In cases in which photo-polymerization is used to cure a resin, a polymerizable monomer of the present disclosure can be used as components in materials applicable many different industries such as transportation (e.g., planes, trains, boats, automobiles, etc.), hobbyist, prototyping, medical, art and design, microfluidics, molds, among others. Such medical devices include, in various embodiments herein, orthodontic appliances.

Synthetic Methods

One of skill in the art may appreciate that any suitable coupling chemistry (e.g., addition or substitution chemistry including Diels-Alder, click chemistry, etc.) can be used to couple the terminal monomers (TM) to the chain of interconnected monomers (monomer chain), and subsequently attach the reactive functional groups to the terminal monomers. Alternatively, it can be envisioned that the reactive functional groups can be attached to a terminal monomer, which is subsequently coupled to the chain of interconnected monomers. Additionally, one of skill in the art may recognize that protecting groups may be necessary for the preparation of certain compounds and may be aware of those conditions compatible with a selected protecting group.

Methods of Forming Polymeric Materials

Further provided herein is a method of polymerizing (e.g., photo-curing) a curable composition (e.g., a photo-curable resin) comprising at least one species of a polymerizable monomer described herein (e.g., those according to Formula (I) or (Ib)), and optionally one or more additional components selected from the group consisting of telechelic polymers, telechelic oligomers, polymerizable monomers (e.g., reactive diluents), polymerization initiators, polymerization inhibitors, solvents, fillers, antioxidants, pigments, colorants, surface modifiers, and mixtures thereof, to obtain an optionally cross-linked polymer, the method comprising a step of mixing the curable composition, optionally after heating, with a reactive diluent before inducing polymerization by heating and/or irradiating the composition; wherein the reactive diluent is selected from the polymerizable monomers, as well as mixtures thereof.

The present disclosure provides methods for producing polymeric materials using curable resins described herein. In various embodiments, provided herein are methods for photo-curing photo-curable resins. Hence, in various instances, provided herein is a method of forming a polymeric material, the method comprising: (i) providing a photo-curable resin of the present disclosure; (ii) exposing the photo-curable resin to a light source; and curing the photo-curable resin to form the polymeric material.

In some embodiments, the photo-curing comprises a single curing step. In some embodiments, the photo-curing comprises a plurality of curing steps. In yet other embodiments, the photo-curing comprises at least one curing step which exposes the curable resin to light. Exposing the curable resin to light can initiate and/or facilitate photopolymerization. In some instances, a photoinitiator can be used as part of the resin to accelerate and/or initiate photopolymerization. In some embodiments, the resin is exposed to UV (ultraviolet) light, visible light, IR (infrared) light, or any combination thereof. In some embodiments, the cured polymeric material is formed from the photo-curable resin using at least one step comprising exposure to a light source, wherein the light source comprises UV light, visible light, and/or IR light. In some embodiments, the light source comprises a wavelength from 10 nm to 200 nm, from 200 nm to 350 nm, from 350 nm to 450 nm, from 450 nm to 550 nm, from 550 nm to 650 nm, from 650 nm to 750 nm, from 750 nm to 850 nm, from 850 nm to 1000 nm, or from 1000 nm to 1500 nm.

In some embodiments, a method of forming a polymeric material from a photo-polymerizable resin described herein can further comprise inducing phase separation in the forming polymeric material (i.e., during photo-curing), wherein such phase separation can be polymerization-induced. The polymerization-induced phase separation can comprise generating one or more polymeric phases in the polymeric material during photo-curing. In some cases, at least one polymeric phase of the one or more polymeric phases is an amorphous polymeric phase. Such at least one amorphous polymeric phase can have a glass transition temperature (Tg) of at least about 40° C., 50° C., 60° C., 80° C., 90° C., 100° C., 110° C. or at least about 120° C. In some cases, at least 25%, 50%, or 75% of polymeric phases generated during photo-curing have a glass transition temperature (Tg) of at least about 40° C., 50° C., 60° C., 80° C., 90° C., 100° C., 110° C. or at least about 120° C. In some instances, at least one polymeric phase that has the glass transition temperature (Tg) of at least about 40° C., 50° C., 60° C., 80° C., 90° C., 100° C., 110° C. or at least about 120° C. comprises, integrated in its polymeric structure (i.e., in a polymerized form), a polymerizable monomer according to Formula (I) or (Ib). In some instances, at least one polymeric phase that has the glass transition temperature (Tg) of at least about 40° C., 50° C., 60° C., 80° C., 90° C., 100° C., 110° C. or at least about 120° C. comprises a polymer that comprises a polymerizable monomer and/or monomer of the present disclosure. In various cases, at least one polymeric phase of the one or more polymeric phases generated during photo-curing comprises a crystalline polymeric material. Hence, in some cases, at least one polymeric phase of the one or more polymeric phases is a crystalline polymeric phase. The crystalline polymeric material (e.g., as part of a crystalline phase) can have a melting point of at least about 40° C., 50° C., 60° C., 80° C., 90° C., 100° C., 110° C. or at least about 120° C.

In some embodiments, a method of forming a polymeric material from a photo-polymerizable resin described herein can further comprise initiating and/or enhancing formation of crystalline phases in the forming polymeric material. In certain embodiments, the triggering comprises cooling the cured material, adding seeding particles to the resin, providing a force to the cured material, providing an electrical charge to the resin, or any combination thereof. In some cases, polymer crystals can yield upon application of a strain (e.g., a physical strain, such as twisting or stretching a material). The yielding may include unraveling, unwinding, disentangling, dislocation, coarse slips, and/or fine slips in the crystallized polymer. In some embodiments, the methods disclosed herein further comprise the step of growing polymer crystals. As described further herein, polymer crystals comprise the crystallizable polymeric material.

Thus, in various embodiments, a method of forming a polymeric material from a photo-polymerizable resin described herein can comprise inducing phase separation in the forming polymeric material (i.e., during photo-curing), wherein such phase separation can yield polymeric materials that comprise one or more amorphous phases, one or more crystalline phases, or both one or more amorphous phases and one or more crystalline phases.

As described herein, a polymeric material produced by the methods provided herein can be characterized by one or more of: (i) a storage modulus greater than or equal to 200 MPa; (ii) a flexural stress of greater than or equal to 1.5 MPa remaining after 24 hours in a wet environment at 37° C.; (iii) an elongation at break greater than or equal to 5% before and after 24 hours in a wet environment at 37° C.; (iv) a water uptake of less than 25 wt % when measured after 24 hours in a wet environment at 37° C.; and (v) transmission of at least 30% of visible light through the polymeric material after 24 hours in a wet environment at 37° C. In various cases, such polymeric material can be characterized by at least 2, 3, 4, or all of these properties.

Fabrication and Use of Orthodontic Appliances

Provided herein are methods for using the polymerizable monomers, curable resins and compositions comprising such compounds, as well as polymeric materials produced from such resins and composition for the fabrication of a medical device, such as an orthodontic appliance (e.g., a dental aligner, a dental expander or a dental spacer).

Thus, in some embodiments, a method herein further comprises the step of fabricating a device or an object using an additive manufacturing device, wherein the additive manufacturing device facilitates the curing. In some embodiments, the curing of a polymerizable resin produces the cured polymeric material. In certain embodiments, a polymerizable resin is cured using an additive manufacturing device to produce the cured polymeric material. In some embodiments, the method further comprises the step of cleaning the cured polymeric material. In certain embodiments, the cleaning of the cured polymeric material includes washing and/or rinsing the cured polymeric material with a solvent, which can remove uncured resin and undesired impurities from the cured polymeric material.

In some embodiments, a polymerizable resin herein can be curable and have melting points <100° C. in order to be liquid and, thus, processable at the temperatures usually employed in currently available additive manufacturing techniques. As described herein, the polymerizable monomers of the present disclosure that are used as components in the curable resins can have a low vapor pressure at an elevated temperature compared to conventional reactive diluents or other polymerizable components used in curable resins. Such low vapor pressure of the monomers described herein can be particularly advantageous for use of such monomer in the curable (e.g., photocurable) compositions and additive manufacturing where elevated temperatures (e.g., 60° C., 80° C., 90° C., or higher) may be used. In various instances, a polymerizable monomer can have a vapor pressure of at most about 12 Pa at 60° C., or lower, as further described herein.

In some embodiments, a curable resin herein can comprise at least one photo-polymerization initiator (i.e., a photoinitiator) and may be heated to a predefined elevated process temperature ranging from about 50° C. to about 120° C., such as from about 90° C. to about 120° C., before becoming irradiated with light of a suitable wavelength to be absorbed by the photoinitiator, thereby causing activation of the photoinitiator to induce polymerization of the curable resin to obtain a cured polymeric material, which an optionally be cross-linked.

In some embodiments, the methods disclosed herein for forming a polymeric material are part of a high temperature lithography-based photo-polymerization process, wherein a curable composition (e.g., a photo-curable resin) that can comprise at least one photo-polymerization initiator is heated to an elevated process temperature (e.g., from about 50° C. to about 120° C., such as from about 90° C. to about 120° C.). Thus, a method for forming a polymeric material according to the present disclosure can offer the possibility of quickly and facilely producing devices, such as orthodontic appliances, by additive manufacturing such as 3D printing using curable resins as disclosed herein. In various embodiments, such curable resin is a photo-curable resin comprising one or more photo-polymerizable monomers described herein.

Photo-polymerization can occur when a photo-curable resin herein is exposed to radiation (e.g., UV or visible light) of a wavelength sufficient to initiate polymerization. The wavelengths of radiation useful to initiate polymerization may depend on the photoinitiator used. “Light” as used herein includes any wavelength and power capable of initiating polymerization. Some wavelengths of light include ultraviolet (UV) or visible. UV light sources include UVA (wavelength about 400 nanometers (nm) to about 320 nm), UVB (about 320 nm to about 290 nm) or UVC (about 290 nm to about 100 nm). Any suitable source may be used, including laser sources. The source may be broadband or narrowband, or a combination thereof. The light source may provide continuous or pulsed light during the process. Both the length of time the system is exposed to UV light and the intensity of the UV light can be varied to determine the ideal reaction conditions.

In some embodiments, the methods disclosed herein include the use of additive manufacturing to produce a device comprising the cured polymeric material. Such device can be an orthodontic appliance. The orthodontic appliance can be a dental aligner, a dental expander or a dental spacer. In certain embodiments, the methods disclosed herein use additive manufacturing to produce a device comprising, consisting essentially of, or consisting of the cured polymeric material. Additive manufacturing includes a variety of technologies which fabricate three-dimensional objects directly from digital models through an additive process. In some aspects, successive layers of material are deposited and "cured in place". A variety of techniques are known to the art for additive manufacturing, including selective laser sintering (SLS), fused deposition modeling (FDM) and jetting or extrusion. In many embodiments, selective laser sintering involves using a laser beam to selectively melt and fuse a layer of powdered material according to a desired cross-sectional shape in order to build up the object geometry. In many embodiments, fused deposition modeling involves melting and selectively depositing a thin filament of thermoplastic polymer in a layer-by-layer manner in order to form an object. In yet another example, 3D printing can be used to fabricate an orthodontic appliance herein. In many embodiments, 3D printing involves jetting or extruding one or more materials (e.g., the crystallizable resins disclosed herein) onto a build surface in order to form successive layers of the object geometry. In some embodiments, a photo-curable resin described herein can be used in inkjet or coating applications. Cured polymeric materials may also be fabricated by "vat" processes in which light is used to selectively cure a vat or reservoir of the curable resin. Each layer of curable resin may be selectively exposed to light in a single exposure or by scanning a beam of light across the layer. Specific techniques that can be used herein can include stereolithography (SLA), Digital Light Processing (DLP) and two photon-induced photo-polymerization (TPIP).

In some embodiments, the methods disclosed herein use continuous direct fabrication to produce a device comprising the cured polymeric material. Such device can be an orthodontic appliance as described herein. In certain embodiments, the methods disclosed herein can comprise the use of continuous direct fabrication to produce a device (e.g., an orthodontic appliance) comprising, consisting essentially of, or consisting of the cured polymeric material. A non-limiting exemplary direct fabrication process can achieve continuous build-up of an object geometry by continuous movement of a build platform (e.g., along the vertical or Z-direction) during an irradiation phase, such that the hardening depth of the irradiated photo-polymer (e.g., an irradiated photo-curable resin, hardening during the formation of a cured polymeric material) is controlled by the movement speed. Accordingly, continuous polymerization of material (e.g., polymerization of a photo-curable resin into a cured polymeric material) on the build surface can be achieved. Such methods are described in U.S. Pat. No. 7,892,474, the disclosure of which is incorporated herein by reference in its entirety. In yet another example, a continuous direct fabrication method utilizes a "heliolithography" approach in which a liquid resin (e.g., a photo-curable resin) is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety. Continuous liquid interface production of 3D objects has also been reported (J. Tumbleston et al., Science, 2015, 347 (6228), pp 1349-1352), which reference is hereby incorporated by reference in its entirety for description of the process. Another example of continuous direct fabrication method can involve extruding a material composed of a curable liquid material or resin surrounding a solid strand. The material can be extruded along a continuous three-dimensional path in order to form the object. Such methods are described in U.S. Patent Publication No. 2014/0061974, the disclosure of which is incorporated herein by reference in its entirety.

In some embodiments, the methods disclosed herein can comprise the use of high temperature lithography to produce a device comprising the cured polymeric material. Such device can be an orthodontic appliance as described herein. In certain embodiments, the methods disclosed herein use high temperature lithography to produce a device comprising, consisting essentially of, or consisting of the cured polymeric material. "High temperature lithography," as used herein, may refer to any lithography-based photo-polymerization processes that involve heating photo-polymerizable material(s) (e.g., a photo-curable resin disclosed herein). The heating may lower the viscosity of the photo-curable resin before and/or during curing. Non-limiting examples of high-temperature lithography processes include those processes described in WO 2015/075094, WO 2016/078838 and WO 2018/032022. In some implementations, high-temperature lithography may involve applying heat to material to temperatures from about 50° C. to about 120° C., such as from about 90° C. to about 120° C., from about 100° C. to about 120° C., from about 105° C. to about 115° C., from about 108° C. to about 110° C., etc. The material may be heated to temperatures greater than about 120° C. It is noted other temperature ranges may be used without departing from the scope and substance of the inventive concepts described herein.

Since, in some cases, the polymerizable monomers of the present disclosure can, as part of a curing process, become co-polymerized in the polymerization process of a method according to the present disclosure, the result can be an optionally cross-linked polymer comprising moieties of one or more species of polymerizable monomer(s) as repeating units. In some cases, such polymer is a cross-linked polymer which, typically, can be suitable and useful for applications in orthodontic appliances. The polymerizable monomers of this disclosure comprising a plurality of reactive functional groups can provide uniform and continuous polymeric networks with clear phase separation.

In further embodiments, a method herein can comprise polymerizing a curable composition which comprises at least one polymerizable monomer, which, upon polymerization, can furnish a cross-linked polymer matrix which can comprise moieties originating from the polymerizable monomer(s) of the present disclosure as repeating units. In order to obtain cross-linked polymers which can be particularly suitable as orthodontic appliances, the at least one polymerizable species used in the method according to the present disclosure can be selected with regard to several thermomechanical properties of the resulting polymers. In some instances, a curable resin of the present disclosure can comprise one or more species of polymerizable monomers. In some cases, a polymerizable monomer of the present disclosure can also have cross-linking functionalities, in instances where it contains a plurality of reactive functional groups (similar to the polymerizable monomers herein), and thus not only act as a reactive diluent with low vapor pressure, but also as a cross-linking agent during polymerization of a curable resin described herein. In other embodiments, a resin comprises a polymerizable monomer as described herein, a polymerizable monomer, and a crosslinking monomer, wherein both monomers are different species (i.e., chemical entities).

VIII. Orthodontic Appliances and Uses Thereof

The polymerizable monomers according to the present disclosure, e.g., those according to Formula (I), can be used as components for viscous or highly viscous photo-curable resins and can result in polymeric materials that can have favorable thermomechanical properties as described herein (e.g., stiffness, stress remaining, etc.) for use in orthodontic appliances, for example, for moving one or more teeth of a patient.

As described herein, the present disclosure provides a method of repositioning a patient's teeth, the method comprising: (i) generating a treatment plan for the patient, the plan comprising a plurality of intermediate tooth arrangements for moving teeth along a treatment path from an initial tooth arrangement toward a final tooth arrangement; (ii) producing a dental appliance comprising a polymeric material described herein, e.g., a polymeric material that comprises, in a polymerized form, compounds according to Formula (I) or (Ib); and moving on-track, with the dental appliance, at least one of the patient's teeth toward an intermediate tooth arrangement or the final tooth arrangement. Such dental appliance can be produced using processes that include 3D printing, as further described herein. The method of repositioning a patient's teeth can further comprise tracking progression of the patient's teeth along the treatment path after administration of the dental appliance to the patient, the tracking comprising comparing a current arrangement of the patient's teeth to a planned arrangement of the patient's teeth. In such instances, greater than 60% of the patient's teeth can be on track with the treatment plan after 2 weeks of treatment. In some instances, the dental appliance has a retained repositioning force to the at least one of the patient's teeth after 2 days that is at least 10%, at least 20%, at least 30%, at least 40%, at least 50%, at least 60%, or at least 70% of repositioning force initially provided to the at least one of the patient's teeth.

As used herein, the terms "rigidity" and "stiffness" can be used interchangeably, as are the corresponding terms "rigid" and "stiff." As used herein a "plurality of teeth" encompasses two or more teeth.

In many embodiments, one or more posterior teeth comprises one or more of a molar, a premolar or a canine, and one or more anterior teeth comprising one or more of a central incisor, a lateral incisor, a cuspid, a first bicuspid or a second bicuspid.

In some embodiments, the compositions and methods described herein can be used to couple groups of one or more teeth to each other. The groups of one or more teeth may comprise a first group of one or more anterior teeth and a second group of one or more posterior teeth. The first group of teeth can be coupled to the second group of teeth with the polymeric shell appliances as disclosed herein.

The embodiments disclosed herein are well suited for moving one or more teeth of the first group of one or more teeth or moving one or more of the second group of one or more teeth, and combinations thereof.

The embodiments disclosed herein are well suited for combination with one or more known commercially available tooth moving components such as attachments and polymeric shell appliances. In many embodiments, the appliance and one or more attachments are configured to move one or more teeth along a tooth movement vector comprising six degrees of freedom, in which three degrees of freedom are rotational and three degrees of freedom are translation.

The present disclosure provides orthodontic systems and related methods for designing and providing improved or more effective tooth moving systems for eliciting a desired tooth movement and/or repositioning teeth into a desired arrangement.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof, for example. In some cases, the reinforced composites can comprise a polymer matrix reinforced with ceramic or metallic particles, for example. The appliance can be shaped in many ways, such as with thermoforming or direct fabrication as described herein, for example. Alternatively, or in combination, the appliance can be fabricated with machining such as an appliance fabricated from a block of material with computer numeric control machining. In some cases, the appliance is fabricated using a polymerizable monomer according to the present disclosure, for example, using the monomers as reactive diluents for curable resins.

Turning now to the drawings, in which like numbers designate like elements in the various figures, FIG. 1A illustrates an exemplary tooth repositioning appliance or aligner 100 that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830, 450.

Figure 1B:
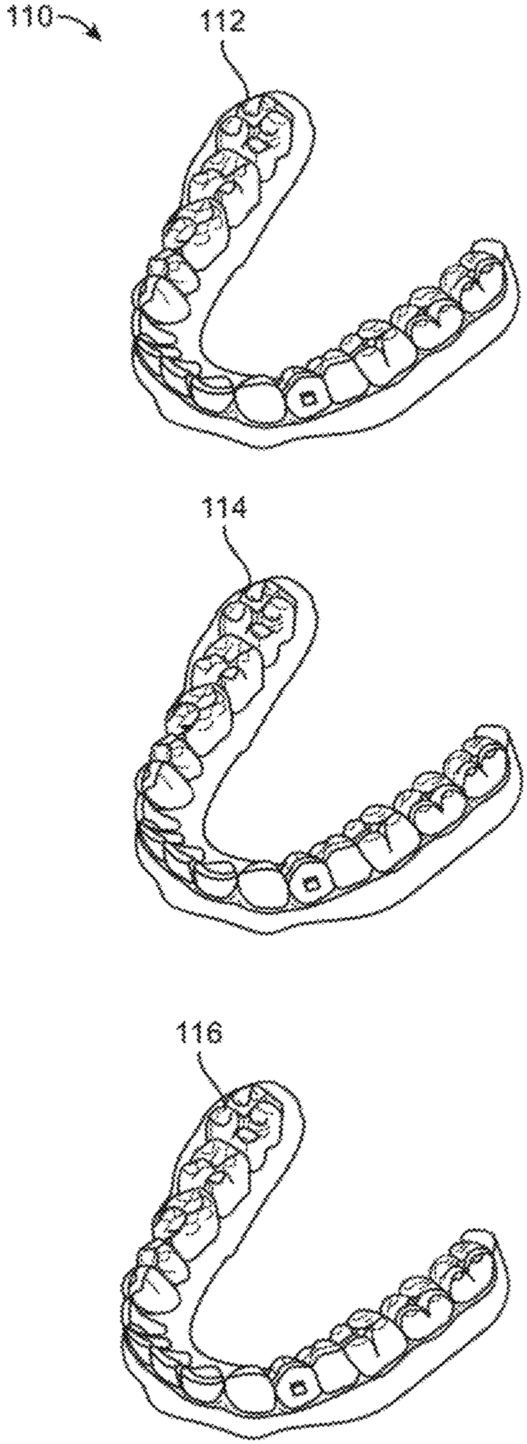
FIG. 1B illustrates a tooth repositioning system, in accordance with embodiments.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 1C:
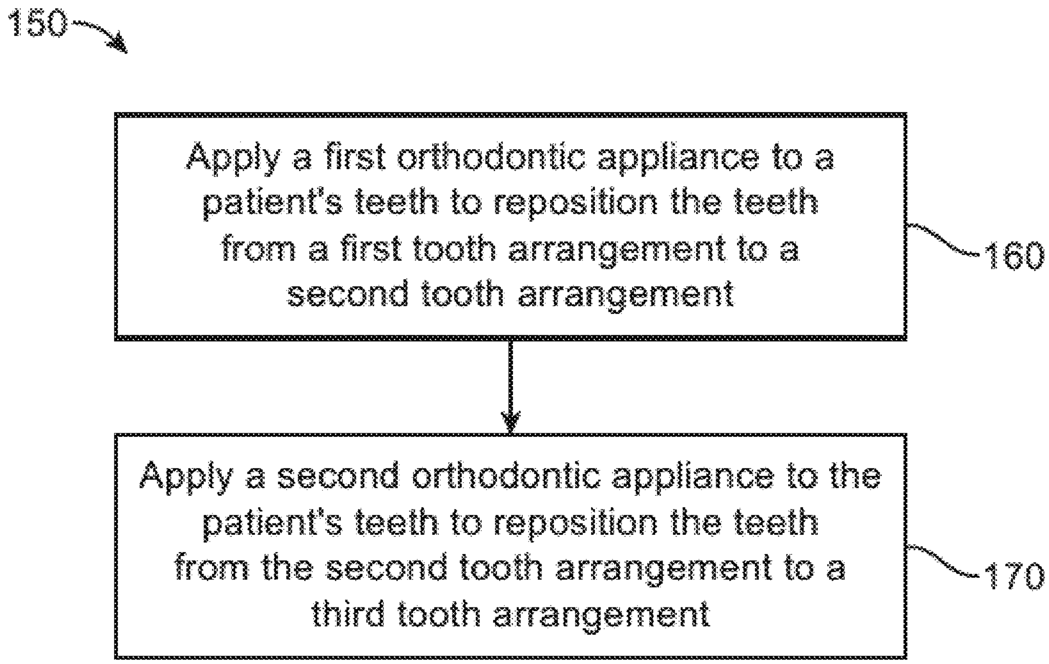
FIG. 1C illustrates a method of orthodontic treatment using a plurality of appliances, in accordance with embodiments.

FIG. 1C illustrates a method 150 of orthodontic treatment using a plurality of appliances, in accordance with embodiments. The method 150 can be practiced using any of the appliances or appliance sets described herein. In step 160, a first orthodontic appliance is applied to a patient's teeth in order to reposition the teeth from a first tooth arrangement to a second tooth arrangement. In step 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing") or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photo-polymerization (e.g., stereolithography), in which an object is constructed layer by layer from a vat of liquid photo-polymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photo-polymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

Alternatively, or in combination, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell.

In some embodiments, the direct fabrication methods provided herein build up the object geometry in a layer-by-layer fashion, with successive layers being formed in discrete build steps. Alternatively, or in combination, direct fabrication methods that allow for continuous build-up of an object geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photo-polymerizable resin by forming a gradient of partially cured resin between the building surface of the object and a polymerization-inhibited "dead zone." In some embodiments, a semi-permeable membrane is used to control transport of a photo-polymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photo-polymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, a thermoset material, or combinations thereof. The materials used for direct fabrication can be provided in an uncured form (e.g., as a liquid, resin, powder, etc.) and can be cured (e.g., by photo-polymerization, light curing, gas curing, laser curing, cross-linking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every nth build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety. Alternatively, or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 μm, or within a range from about 5 μm to about 50 μm, or within a range from about 20 μm to about 50 μm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variability in appliance thickness and/or other properties.

Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

Figure 2:
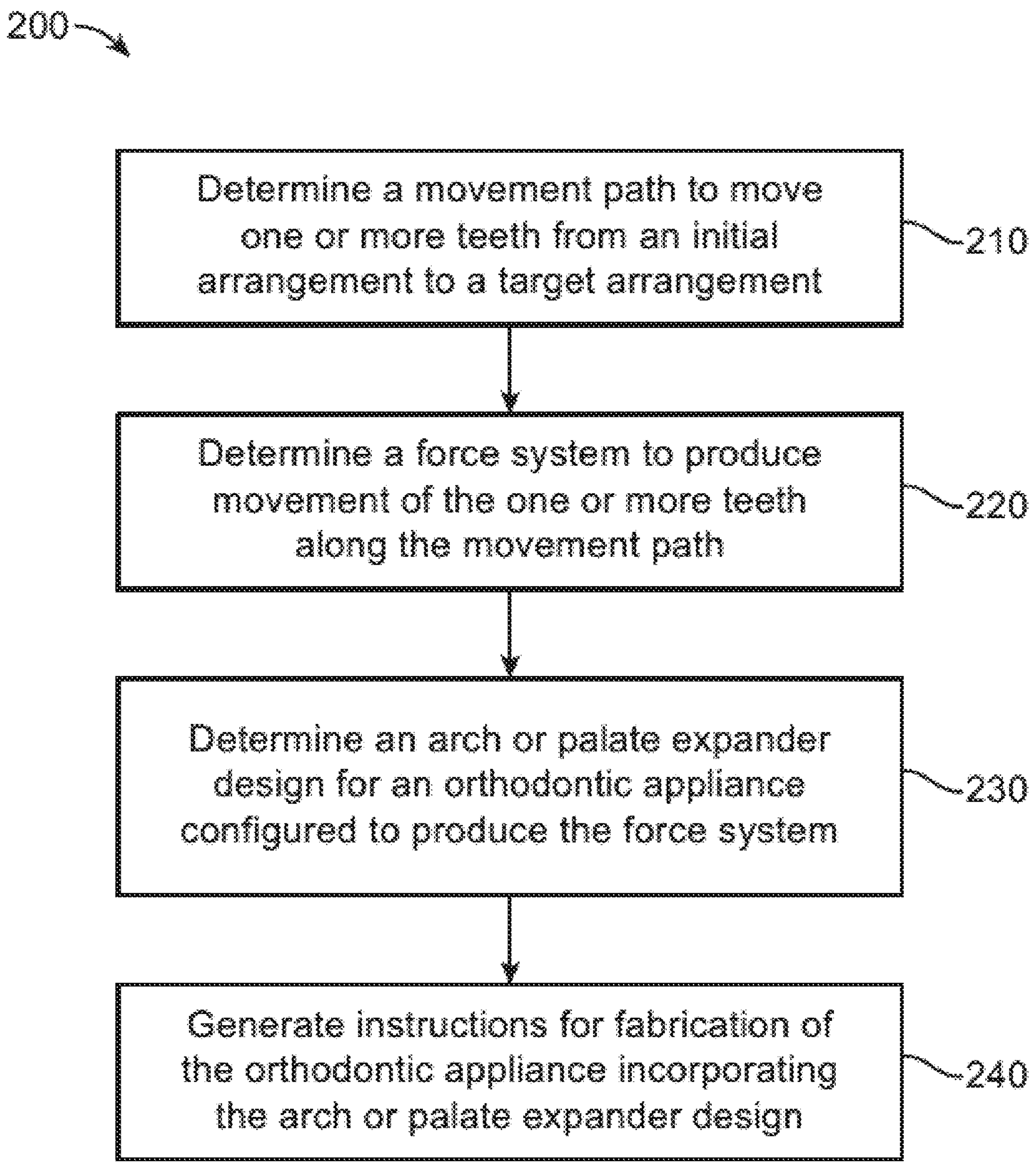
FIG. 2 illustrates a method for designing an orthodontic appliance, in accordance with embodiments.

FIG. 2 illustrates a method 200 for designing an orthodontic appliance to be produced by direct fabrication, in accordance with embodiments. The method 200 can be applied to any embodiment of the orthodontic appliances described herein. Some or all of the steps of the method 200 can be performed by any suitable data processing system or device, e.g., one or more processors configured with suitable instructions.

In step 210, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In step 220, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces. These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as Xray data or 3D optical scanning data, for example, can be used to determine parameters of the skeletal and muscular system of the patient's mouth, so as to determine forces sufficient to provide a desired expansion of the palate and/or arch. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients will typically require lower forces to expand the suture than older patients, as the suture has not yet fully formed.

In step 230, an arch or palate expander design for an orthodontic appliance configured to produce the force system is determined. Determination of the arch or palate expander design, appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, CA For creating finite element models and analyzing them, program products from a number of vendors can be used, including finite element analysis packages from ANSYS, Inc., of Canonsburg, PA, and SIMULIA(Abaqus) software products from Dassault Systemes of Waltham, MA Optionally, one or more arch or palate expander designs can be selected for testing or force modeling. As noted above, a desired tooth movement, as well as a force system required or desired for eliciting the desired tooth movement, can be identified. Using the simulation environment, a candidate arch or palate expander design can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In step 240, instructions for fabrication of the orthodontic appliance incorporating the arch or palate expander design are generated. The instructions can be configured to control a fabrication system or device in order to produce the orthodontic appliance with the specified arch or palate expander design. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by thermoforming.

Method 200 may comprise additional steps: 1) The upper arch and palate of the patient is scanned intraorally to generate three dimensional data of the palate and upper arch; 2) The three dimensional shape profile of the appliance is determined to provide a gap and teeth engagement structures as described herein.

Although the above steps show a method 200 of designing an orthodontic appliance in accordance with some embodiments, a person of ordinary skill in the art will recognize some variations based on the teaching described herein. Some of the steps may comprise sub-steps. Some of the steps may be repeated as often as desired. One or more steps of the method 200 may be performed with any suitable fabrication system or device, such as the embodiments described herein. Some of the steps may be optional, and the order of the steps can be varied as desired.

Figure 3:
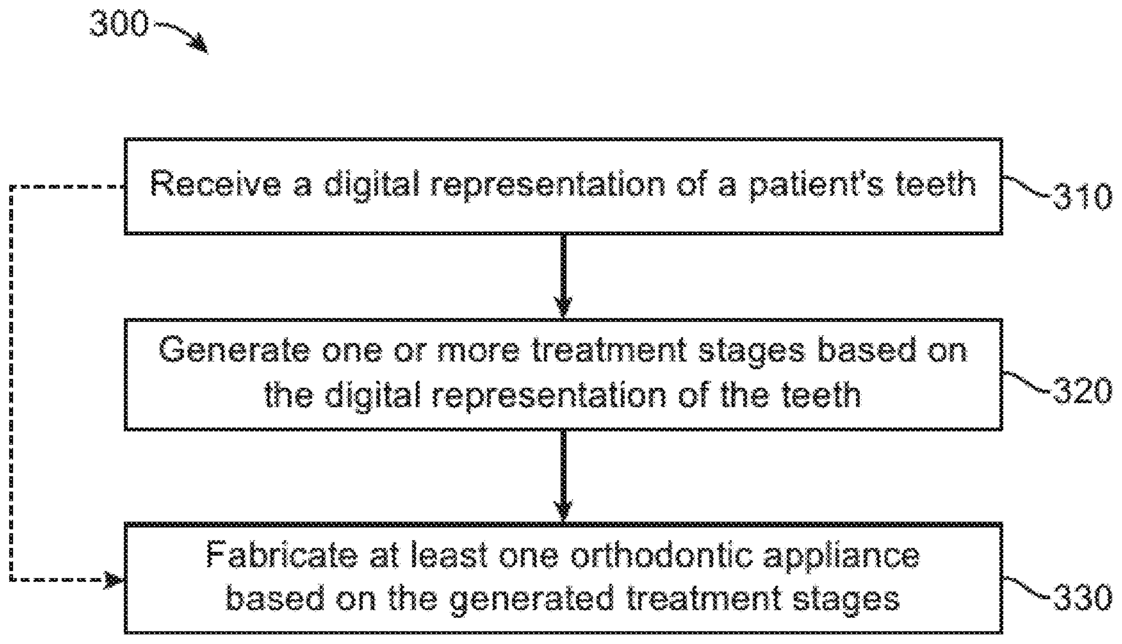
FIG. 3 illustrates a method for digitally planning an orthodontic treatment, in accordance with embodiments.

FIG. 3 illustrates a method 300 for digitally planning an orthodontic treatment and/or design or fabrication of an appliance, in accordance with embodiments. The method 300 can be applied to any of the treatment procedures described herein and can be performed by any suitable data processing system.

In step 310, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step 320, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step 330, at least one orthodontic appliance is fabricated based on the generated treatment stages. For example, a set of appliances can be fabricated, each shaped according a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 3, design and/or fabrication of an orthodontic appliance, and perhaps a particular orthodontic treatment, may include use of a representation of the patient's teeth (e.g., receive a digital representation of the patient's teeth 310), followed by design and/or fabrication of an orthodontic appliance based on a representation of the patient's teeth in the arrangement represented by the received representation.

On-Track Treatment

Figure 4:
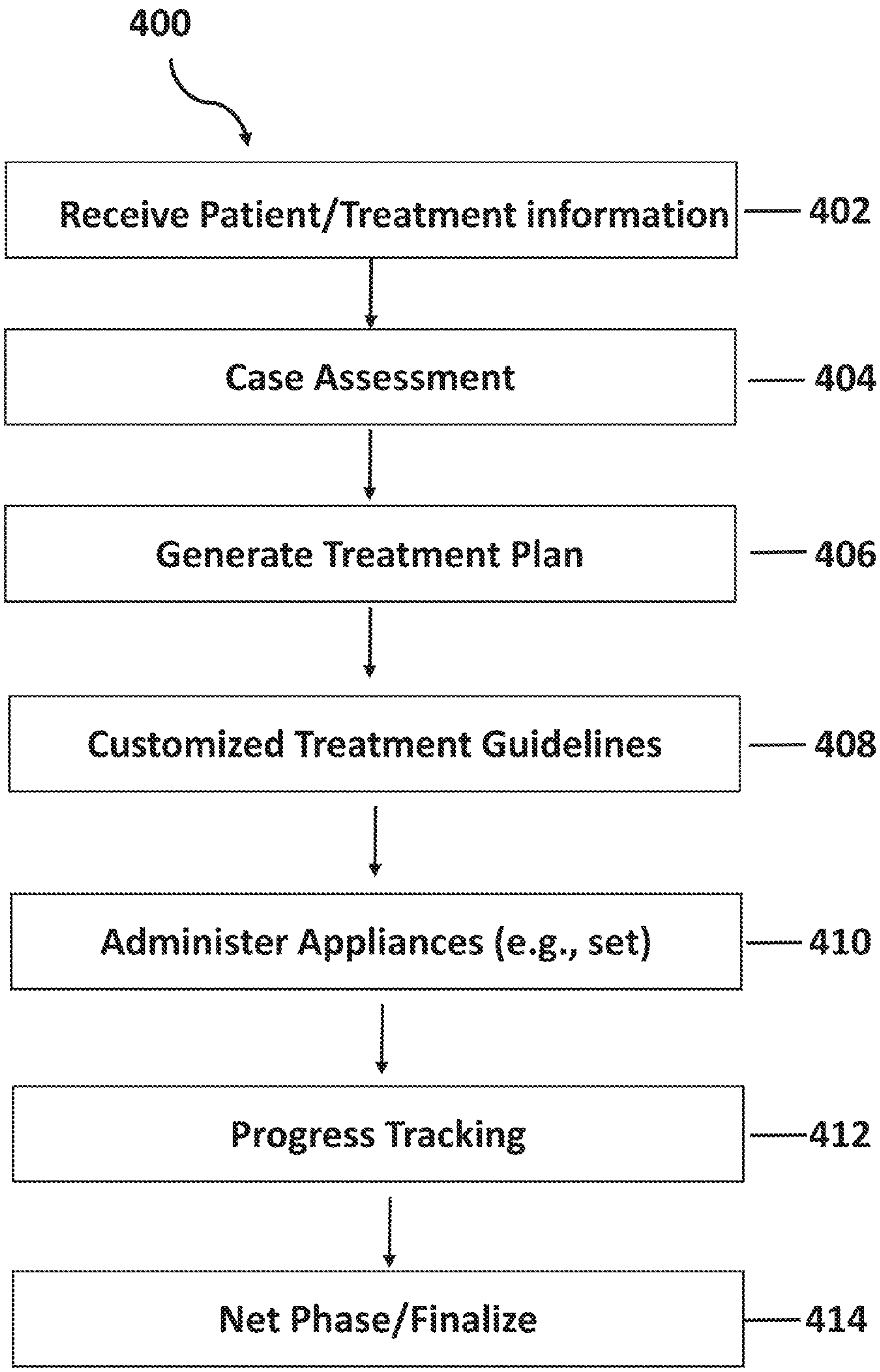
FIG. 4 shows generating and administering treatment according to an embodiment of the present disclosure.

Referring to FIG. 4, a process 400 according to the present disclosure is illustrated. Individual aspects of the process are discussed in further detail below. The process includes receiving information regarding the orthodontic condition of the patient and/or treatment information (402), generating an assessment of the case (404), and generating a treatment plan for repositioning a patient's teeth (406). Briefly, a patient/treatment information includes data comprising an initial arrangement of the patient's teeth, which includes obtaining an impression or scan of the patient's teeth prior to the onset of treatment and can further include identification of one or more treatment goals selected by the practitioner and/or patient. A case assessment can be generated (404) so as to assess the complexity or difficulty of moving the particular patient's teeth in general or specifically corresponding to identified treatment goals, and may further include practitioner experience and/or comfort level in administering the desired orthodontic treatment. In some cases, however, the assessment can include simply identifying particular treatment options (e.g., appointment planning, progress tracking, etc.) that are of interest to the patient and/or practitioner. The information and/or corresponding treatment plan includes identifying a final or target arrangement of the patient's teeth that is desired, as well as a plurality of planned successive or intermediary tooth arrangements for moving the teeth along a treatment path from the initial arrangement toward the selected final or target arrangement.

The process further includes generating customized treatment guidelines (408). The treatment plan may include multiple phases of treatment, with a customized set of treatment guidelines generated that correspond to a phase of the treatment plan. The guidelines can include detailed information on timing and/or content (e.g., specific tasks) to be completed during a given phase of treatment, and can be of sufficient detail to guide a practitioner, including a less experienced practitioner or practitioner relatively new to the particular orthodontic treatment process, through the phase of treatment. Since the guidelines are designed to specifically correspond to the treatment plan and provide guidelines on activities specifically identified in the treatment information and/or generated treatment plan, the guidelines can be customized. The customized treatment guidelines are then provided to the practitioner so as to help instruct the practitioner as how to deliver a given phase of treatment. As set forth above, appliances can be generated based on the planned arrangements and can be provided to the practitioner and ultimately administered to the patient (410). The appliances can be provided and/or administered in sets or batches of appliances, such as 2, 3, 4, 5, 6, 7, 8, 9, or more appliances, but are not limited to any particular administrative scheme. Appliances can be provided to the practitioner concurrently with a given set of guidelines, or appliances and guidelines can be provided separately.

After the treatment according to the plan begins and following administration of appliances to the patient, treatment progress tracking, e.g., by teeth matching, is done to assess a current and actual arrangement of the patient's teeth compared to a planned arrangement (412). If the patient's teeth are determined to be "on-track" and progressing according to the treatment plan, then treatment progresses as planned and treatment progresses to the next stage of treatment (414). If the patient's teeth have substantially reached the initially planned final arrangement, then treatment progresses to the final stages of treatment (414). Where the patient's teeth are determined to be tracking according to the treatment plan, but have not yet reached the final arrangement, the next set of appliances can be administered to the patient.

The threshold difference values of a planned position of teeth to actual positions selected as indicating that a patient's teeth have progressed on-track are provided below in TABLE 1. If a patient's teeth have progressed at or within the threshold values, the progress is considered to be on-track. If a patient's teeth have progressed beyond the threshold values, the progress is considered to be off-track.

TABLE 1

| Type Movement | Difference Actual/Planned |
|---|---|
| Rotations | |
| Upper Central Incisors | 9 degrees |
| Upper Lateral Incisors | 11 degrees |
| Lower Incisors | 11 degrees |
| Upper Cuspids | 11 degrees |
| Lower Cuspids | 9.25 degrees |
| Upper Bicuspids | 7.25 degrees |
| Lower First Bicuspid | 7.25 degrees |
| Lower Second Bicuspid | 7.25 degrees |
| Molars | 6 degrees |
| Extrusion | |
| Anterior | 0.75 mm |
| Posterior | 0.75 mm |
| Intrusion | |
| Anterior | 0.75 mm |
| Posterior | 0.75 mm |
| Angulation | |
| Anterior | 5.5 degrees |
| Posterior | 3.7 degrees |
| Inclination | |
| Anterior | 5.5 degrees |
| Posterior | 3.7 degrees |
| Translation | |
| BL Anterior | 0.7 mm |
| BL Posterior Cuspids | 0.9 mm |
| MD Anterior | 0.45 mm |
| MD Cuspids | 0.45 mm |
| MD Posterior | 0.5 mm |

The patient's teeth are determined to be on track by comparison of the teeth in their current positions with teeth in their expected or planned positions, and by confirming the teeth are within the parameter variance disclosed in TABLE 1. If the patient's teeth are determined to be on track, then treatment can progress according to the existing or original treatment plan. For example, a patient determined to be progressing on track can be administered one or more subsequent appliances according to the treatment plan, such as the next set of appliances. Treatment can progress to the final stages and/or can reach a point in the treatment plan where bite matching is repeated for a determination of whether a patient's teeth are progressing as planned or if the teeth are off track.

In some embodiments, as further disclosed herein, this disclosure provides methods of treating a patient using a 3D printed orthodontic appliance. As a non-limiting example, orthodontic appliances comprising crystalline domains, polymer crystals, and/or materials that can form crystalline domains or polymer crystals can be 3D printed and used to reposition a patient's teeth. In certain embodiments, the method of repositioning a patient's teeth (or, in some embodiments, a singular tooth) comprises: generating a treatment plan for the patient, the plan comprising a plurality of intermediate tooth arrangements for moving teeth along a treatment path from an initial arrangement toward a final arrangement; producing a 3D printed orthodontic appliance; and moving on-track, with the orthodontic appliance, at least one of the patient's teeth toward an intermediate arrangement or a final tooth arrangement. In some embodiments, producing the 3D printed orthodontic appliance uses the crystallizable resins disclosed further herein. On-track performance can be determined, e.g., from TABLE 1, above.

In some embodiments, the method further comprises tracking the progression of the patient's teeth along the treatment path after administration of the orthodontic appliance. In certain embodiments, the tracking comprises comparing a current arrangement of the patient's teeth to a planned arrangement of the teeth. As a non-limiting example, following the initial administration of the orthodontic appliance, a period of time passes (e.g., two weeks), a comparison of the now-current arrangement of the patient's teeth (i.e., at two weeks of treatment) can be compared with the teeth arrangement of the treatment plan. In some embodiments, the progression can also be tracked by comparing the current arrangement of the patient's teeth with the initial configuration of the patient's teeth. The period of time can be, for example, greater than 3 days, greater than 4 days, greater than 5 days, greater than 6 days, greater than 7 days, greater than 8 days, greater than 9 days, greater than 10 days, greater than 11 days, greater than 12 days, greater than 13 days, greater than 2 weeks, greater than 3 weeks, greater than 4 weeks, or greater than 2 months. In some embodiments, the period of time can be from at least 3 days to at most 4 weeks, from at least 3 days to at most 3 weeks, from at least 3 days to at most 2 weeks, from at least 4 days to at most 4 weeks, from at least 4 days to at most 3 weeks, or from at least 4 days to at most 2 weeks. In certain embodiments, the period of time can restart following the administration of a new orthodontic appliance.

In some embodiments, greater than 50%, greater than 55%, greater than 60%, greater than 65%, greater than 70%, greater than 75%, greater than 80%, greater than 85%, greater than 90%, greater than 91%, greater than 92%, greater than 93%, greater than 94%, greater than 95%, greater than 96%, greater than 97%, greater than 98%, or greater than 99% of the patient's teeth are on track with the treatment plan after a period of time of using an orthodontic appliance as disclosed further herein. In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

As disclosed further herein, orthodontic appliances disclosed herein have advantageous properties, such as increased durability, and an ability to retain resilient forces to a patient's teeth for a prolonged period of time. In some embodiments of the method disclosed above, the 3D printed orthodontic appliance has a retained repositioning force (i.e., the repositioning force after the orthodontic appliance has been applied to or worn by the patient over a period of time), and the retained repositioning force to at least one of the patient's teeth after the period of time is at least 10%, at least 20%, at least 30%, at least 40%, at least 50%, at least 55%, at least 60%, at least 65%, at least 70%, at least 75%, at least 80%, at least 85%, at least 90%, at least 95%, at least 96%, at least 97%, at least 98%, or at least 99% of the repositioning force initially provided to the at least one of the patient's teeth (i.e., with initial application of the orthodontic appliance). In some embodiments, the period of time is 1 day, 2 days, 3 days, 4 days, 5 days, 6 days, 7 days, 8 days, 9 days, 10 days, 11 days, 12 days, 13 days, 2 weeks, 3 weeks, 4 weeks, or greater than 4 weeks. In some embodiments, the repositioning force applied to at least one of the patient's teeth is present for a time period of less than 24 hours, from about 24 hours to about 2 months, from about 24 hours to about 1 month, from about 24 hours to about 3 weeks, from about 24 hours to about 14 days, from about 24 hours to about 7 days, from about 24 hours to about 3 days, from about 3 days to about 2 months, from about 3 days to about 1 month, from about 3 days to about 3 weeks, from about 3 days to about 14 days, from about 3 days to about 7 days, from about 7 days to about 2 months, from about 7 days to about 1 month, from about 7 days to about 3 weeks, from about 7 days to about 2 weeks, or greater than 2 months. In some embodiments, the repositioning force applied to at least one of the patient's teeth is present for about 24 hours, for about 3 days, for about 7 days, for about 14 days, for about 2 months, or for more than 2 months.

In some embodiments, the orthodontic appliances disclosed herein can provide on-track movement of at least one of the patient's teeth. On-track movement has been described further herein, e.g., at TABLE 1. In some embodiments, the orthodontic appliances disclosed herein can be used to achieve on-track movement of at least one of the patient's teeth to an intermediate tooth arrangement. In some embodiments, the orthodontic appliances disclosed herein can be used to achieve on-track movement of at least one of the patient's teeth to a final tooth arrangement.

In some embodiments, prior to moving, with the orthodontic appliance, at least one of the patient's teeth toward an intermediate arrangement or a final tooth arrangement, the orthodontic appliance has characteristics which are retained following the use of the orthodontic appliance. In some embodiments, prior to the moving step, the orthodontic appliance comprises a first flexural modulus. In certain embodiments, after the moving step, the orthodontic appliance comprises a second flexural modulus. In some embodiments, the second flexural modulus is at least 99%, at least 98%, at least 97%, at least 96%, at least 95%, at least 94%, at least 93%, at least 92%, at least 91%, at least 90%, at least 85%, at least 80%, at least 75%, at least 70%, at least 65%, at least 60%, at least 50%, or at least 40% of the first flexural modulus. In some embodiments, the second flexural modulus is greater than 50% of the first flexural modulus. In some embodiments, this comparison is performed following a period of time in which the appliance is applied. In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

In some embodiments, prior to the moving step, the orthodontic appliance comprises a first elongation at break. In certain embodiments, after the moving step, the orthodontic appliance comprises a second elongation at break. In some embodiments, the second elongation at break is at least 99%, at least 98%, at least 97%, at least 96%, at least 95%, at least 94%, at least 93%, at least 92%, at least 91%, at least 90%, at least 85%, at least 80%, at least 75%, at least 70%, at least 65%, at least 60%, at least 50%, or at least 40% of the first elongation at break. In some embodiments, the second elongation at break is greater than 50% of the first elongation at break. In some embodiments, this comparison is performed following a period of time in which the appliance is applied. In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

As provided herein, the methods disclosed can use the orthodontic appliances further disclosed herein. The orthodontic appliances can be directly fabricated using, e.g., the crystallizable resins disclosed herein. In certain embodiments, the direct fabrication comprises cross-linking the crystallizable resin.

The appliances formed from the crystallizable resins disclosed herein provide improved durability, strength, and flexibility, which in turn improve the rate of on-track progression in treatment plans. In some embodiments, greater than 60%, greater than 70%, greater than 80%, greater than 90%, or greater than 95% of patients treated with the orthodontic appliances disclosed herein (e.g., an aligner) are classified as on-track in a given treatment stage. In certain embodiments, greater than 60%, greater than 70%, greater than 80%, greater than 90%, or greater than 95% of patients treated with the orthodontic appliances disclosed herein (e.g., an aligner) have greater than 50%, greater than 55%, greater than 60%, greater than 65%, greater than 70%, greater than 75%, greater than 80%, greater than 85%, greater than 90%, or greater than 95% of their tooth movements classified as on-track.

As disclosed further herein, the cured polymeric material contains favorable characteristics that, at least in part, stem from the presence of polymeric crystals. These cured polymeric materials can have increased resilience to damage, can be tough, and can have decreased water uptake when compared to similar polymeric materials. The cured polymeric materials can be used for devices within the field of orthodontics, as well as outside the field of orthodontics. For example, the cured polymeric materials disclosed herein can be used to make devices for use in aerospace applications, automobile manufacturing, the manufacture of prototypes, and/or devices for use in durable parts production.

IX. Experimental Methods

All chemicals were purchased from commercial sources and were used without further purification, unless otherwise stated.

1H NMR and 13C NMR spectra were recorded on a BRUKER AC-E-200 FT-NMR spectrometer or a BRUKER Avance DRX-400 FT-NMR spectrometer. The chemical shifts are reported in ppm (s: singlet, d: doublet, t: triplet, q: quartet, m: multiplet). The solvents used were deuterated chloroform ($CDCl_3$, 99.5% deuteration) and deuterated DMSO (d6 DMSO, 99.8% deuteration).

In some embodiments, the stress relaxation of a material or device can be measured by monitoring the time-dependent stress resulting from a steady strain. The extent of stress relaxation can also depend on the temperature, relative humidity and other applicable conditions (e.g., presence of water). In embodiments, the test conditions for stress relaxation are a temperature of 37±2° C. at 100% relative humidity or a temperature of 37±2° C. in water.

The dynamic viscosity of a fluid indicates its resistance to shearing flows. The SI unit for dynamic viscosity is the Poiseuille (Pa s). Dynamic viscosity is commonly given in units of centipoise, where 1 centipoise (cP) is equivalent to 1 mPa s. Kinematic viscosity is the ratio of the dynamic viscosity to the density of the fluid; the SI unit is $m^2/s$. Devices for measuring viscosity include viscometers and rheometers. For example, an MCR 301 rheometer from Anton Paar may be used for rheological measurement in rotation mode (PP-25, 50 s-1, 50-115° C., 3° C./min).

Determining the water content when fully saturated at use temperature can comprise exposing the polymeric material to 100% humidity at the use temperature (e.g., 40° C.) for a period of 24 hours, then determining water content by methods known in the art, such as by weight.

In some embodiments, the presence of a crystalline phase and an amorphous phase provide favorable material properties to the polymeric materials. Property values of the cured polymeric materials can be determined, for example, by using the following methods:

stress relaxation properties can be assessed using an RSA-G2 instrument from TA Instruments, with a 3-point bending, according to ASTM D790; for example, stress relaxation can be measured at 30° C. and submerged in water, and reported as the remaining load after 24 hours, as either the percent (%) of initial load, and/or in MPa;

storage modulus can be measured at 37° C. and is reported in MPa;

Tg of the cured polymeric material can be assessed using dynamic mechanical analysis (DMA) and is provided herein as the tan δ peak;

tensile modulus, tensile strength, elongation at yield and elongation at break can be assessed according to ISO 527-2 5B; and tensile strength at yield, elongation at break, tensile strength, and Young's modulus can be assessed according to ASTM D1708.

Figure 6:
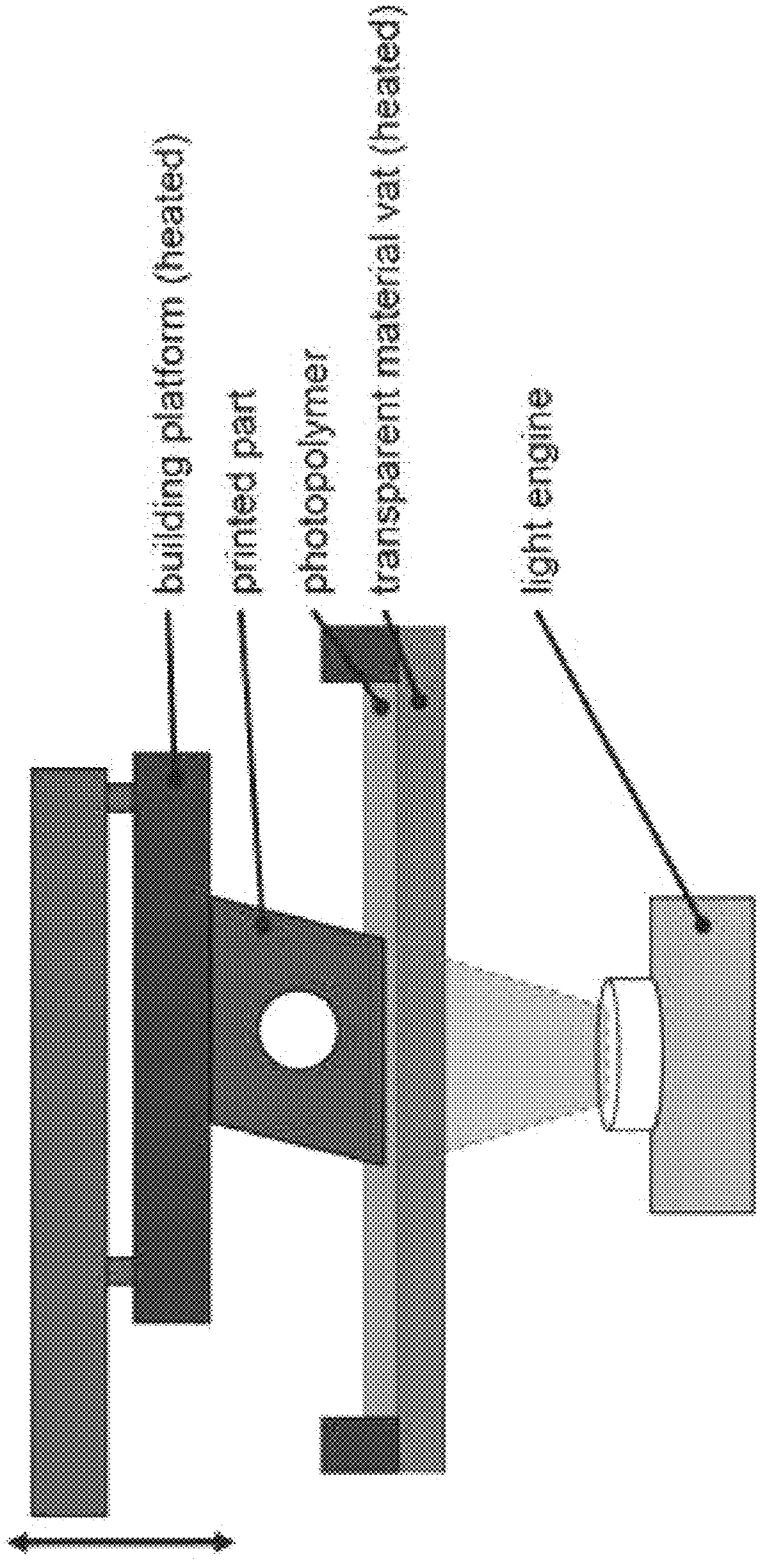
FIG. 6 shows a schematic configuration of an (e.g., high temperature) additive manufacturing device used for curing a curable composition of the present disclosure by using a 3D printing process.

Additive manufacturing or 3D printing processes for generating a device herein (e.g., an orthodontic appliance) can be conducted using a Hot Lithography apparatus prototype from Cubicure (Vienna, Austria), which can substantially be configured as schematically shown in FIG. 6. In such cases, a photo-curable composition (e.g., resin) according to the present disclosure can be filled into the transparent material vat of the apparatus shown in FIG. 6, which vat can be heated to 90-110° C. The building platform can be heated to 90-110° C., too, and lowered to establish holohedral contact with the upper surface of the curable composition. By irradiating the composition with 375 nm UV radiation using a diode laser from Soliton, which can have an output power of 70 mW, which can be controlled to trace a predefined prototype design, and alternately raising the building platform, the composition can be cured layer by layer by a photopolymerization process according to the disclosure, resulting in a polymeric material according to present disclosure

EXAMPLES

The specific compositions, synthesis, formulations, and descriptions of any of the materials, devices, systems, and components thereof, of the present disclosure can be readily varied depending upon the intended application, as will be apparent to those of skill in the art in view of the disclosure herein. Moreover, it is understood that the examples and aspects described herein are for illustrative purposes only and that various modifications or changes in light thereof can be suggested to persons skilled in the art and are included within the spirit and purview of this application and scope of the appended claims. Numerous different combinations of aspects described herein are possible, and such combinations are considered part of the present disclosure. In addition, all features discussed in connection with any one aspect herein can be readily adapted for use in other aspects herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

Example 1

Synthesis and Characterization of Para-Tertiary Alkyl Syringyl Acrylates and Methacrylates This example covers synthesis and characterization of a set of syringyl acrylate and syringyl methacrylate compounds. The two-step synthesis involves Friedel-Crafts alkylation of 2,6-dimethoxyphenol with a tertiary alcohol (HO—C($R^2$)($R^3$)($R^4$)) followed by esterification using an acrylic or a methacrylic anhydride (Scheme 2). Syringyl acrylate, syringyl methacrylate, 4-(t-butyl)-syringyl acrylate, 4(t-butyl)-syringyl methacrylate, 4-(t-pentyl)-syringyl methacrylate, 4-(3-ethylpentan-3-yl)-syringyl methacrylate, and 4-(1-methylcyclohexyl)-syringyl methacrylate were synthesized according to this procedure.

Scheme 2

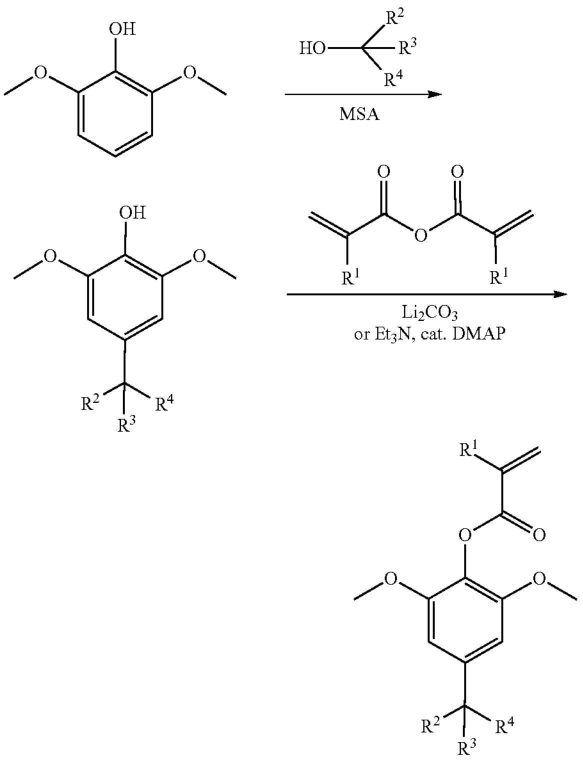

A general procedure for the synthesis of 4-(t-butyl)-syringyl methacrylate is provided herein: To a 250-mL round-bottom flask equipped with a magnetic stir bar were added syringol (25.0 g, 0.162 mol) and t-butanol (16.2 mL, 0.160 mol). The mixture was heated to 50° C. while stirring to dissolve syringol. Then, the flask was cooled in an ice-water bath before methanesulfonic acid (42.1 mL, 0.649 mol) was added. The reaction mixture was allowed to stir at 0° C. and slowly warm to room temperature over 3 h. Then, the reaction as allowed to continue stirring at room temperature overnight. The mixture was poured onto ice and extracted with dichloromethane. The organic layer was washed with water and saturated sodium bicarbonate solution, dried over magnesium sulfate, and concentrated in vacuo, yielding the expected alkylated phenol intermediate (33.6 g, 98.5% yield) as a brown liquid. The intermediate was combined with methacrylic anhydride (26.2 mL, 0.176 mol), triethylamine (24.5 mL, 0.176 mol), dimethylaminopropylamine (1.95 g, 0.016 mol), and chloroform (160 mL) in a 500-mL round-bottom flask equipped with a magnetic stir bar, and the mixture was sparged with nitrogen gas for 15 minutes. The reaction was heated to 50° C. and allowed to stir at 50° C. overnight. The mixture was then cooled and concentrated. The crude product was passed through a silica gel column eluting with 25% ethyl acetate/75% hexanes and recrystallized from hexanes to yield 4-(t-butyl)-syringyl methacrylate as a white crystalline solid (28 g, 63% yield).

The resulting 4-(tertiary alkyl)-2,6,-dimethoxylphenyl acrylates and methacrylates exhibited low vapor pressures, can be liquids or crystalline solids at room temperature, and are capable of forming high-glass transition temperature (Tg) polymers. The melting points of the five synthesized compounds are listed in TABLE 2, in which $R^1$ and $C(R^2)(R^3)(R^4)$ reflect substituents in Scheme 2, or with H in place of $—C(R^2)(R^3)(R^4)$.

TABLE 2

Melting Points of Para-Tertiary Alkyl Syringyl Acrylates and Methacrylates

| Compound Name | $R^1$ | H or $—C(R^2)(R^3)(R^4)$ | Melting Point (° C.) |
|---|---|---|---|
| Syringyl acrylate | H | H | N/A |
| Syringyl methacrylate | Me | H | 39-41 |
| 4-(t-butyl)-syringyl acrylate | H | $CMe_3$ | 120-122 |
| 4-(t-butyl)-syringyl methacrylate | Me | $CMe_3$ | 114-115 |
| 4-(t-pentyl)-syringyl methacrylate | Me | $C(CH_3)_2(CH_2CH_3)$ | 78-80 |
| 4-(3-ethylpentan-3-yl)-syringyl methacrylate | Me | $C(Et)_3$ | 71-72 |
| 4-(1-methylcyclohexyl)-syringyl methacrylate | Me | $C(CH_3)(Cy)$ | 99-100 |

As outlined in TABLE 2, para-tertiary alkyl substitution increases the melting point of acrylates and methacrylates. While syringyl methacrylate melts between 39 and 41° C., and syringyl acrylate is liquid at room temperature, 4-(t-butyl)-syringyl methacrylate and 4-(t-butyl)-syringyl acrylate have melting points of between 114 and 122° C., reflecting 30 to greater than 100° C. increases in melting point.

Example 2

Cured Formulations with Para-Tertiary Alkyl Syringyl Methacrylates

This example covers formulations and physical properties of photo-cured resins containing varying amounts of para-tertiary alkyl syringyl methacrylates. A total of three cured formulations were compared. Each formulation contained 7-8% (w/w) of 2 kDa polytetrahydrofuran (PTHF), 1% (w/w) TPO, and 29-33% (w/w) of an oligomer. The formulations varied in terms of para tertiary alkyl-substituted and para tertiary alkyl-non substituted syringyl acrylate and methacrylate concentrations, with formulations 1 and 2 containing even amounts of the para tertiary alkyl substituted and unsubstituted syringyl acrylates or methacrylates, and formulation 3 containing only para tertiary alkyl substituted methacrylate. The compositions and casting temperatures of each formulation are summarized in TABLE 3 below, with DYMAX XCAC-24-142 corresponding to a urethane-containing polymer with a molecular weight between 6 and 10 kDa, and containing segments of low-$T_g$ (e.g., PTHF with $T_g$=−80° C.) polyether, and polymerizable end groups (e.g., acrylates or methacrylates.

TABLE 3

| Photocured Para-Tertiary Alkyl Syringyl Methacrylate Formulations | | | | |
|---|---|---|---|---|
| | FORMULATION 0 | FORMULATION 1 | FORMULATION 2 | FORMULATION 3 |
| Casting Temperature | 80° C. | 95° C. | 95° C. | 80° C. |
| DYMAX XCAC-24-142 | 36 wt % | 30 wt % | 33 wt % | 29 wt % |
| Syringyl methacrylate | 55 wt % | 31 wt % | 29 wt % | — |
| 4-(t-butyl)-syringyl methacrylate | — | 31 wt % | — | — |
| Homosalic methacrylate | — | — | 29 wt % | — |
| (1,1'-Biphenyl)-2-yl methacrylate | — | — | — | 64 wt % |
| 4-(3-Ethylpentan-3-yl)-syringyl methacrylate | — | 8 wt % | 8 wt % | 7 wt % |
| $PTHF_{2k}$, f = 4 | 9 wt % | 1 wt % | 1 wt % | 1 wt % |

Photo-curable para-(tertiary alkyl)-syringyl methacrylates, when utilized as a major component in a photo-curable resin along with low Tg-oligomers, induced controllable phase separation during curing. The properties of the resultant materials are summarized in TABLE 4. Each material exhibited high toughness, as well as tensile, flexural, and thermomechanical strength.

TABLE 4

| Properties of Cured Para-Tertiary Alkyl Syringyl Methacrylate Resins | | | | |
|---|---|---|---|---|
| PROPERTY | FORMULATION 0 | FORMULATION 1 | FORMULATION 2 | FORMULATION 3 |
| Young's mod. @ 1.7 mm/min [MPa] | 946 | 1231 | 1281 | 1272 |
| Young's mod. @ 510 mm/min [MPa] | 1147 | 1600 | 1641 | 1618 |
| EoB @ 1.7 mm/min [%] | 98 | 85 | 103 | 69 |
| EoB @ 510 mm/min [%] | 47 | 40 | 49 | 16 |
| Yield stress @ 1.7 mm/min [MPa] | 26.9 | 28.1 | 29.5 | 31.8 |
| Yield stress @ 510 mm/min [MPa] | 37.9 | 43.3 | 46.3 | 48.9 |
| 24 Hr flexural modulus [MPa] | 169 | 79 | 86 | 111 |
| Stress remaining [%] | 24 | 11 | 13 | 14 |
| 24 Hr force [N] | 4.0 | 1.7 | 2.1 | 2.6 |
| Tg − tan delta [° C.] | >150 | 104 | 106 | 120 |

Example 3

Treatment Using an Orthodontic Appliance

This example describes the use of a directly 3D printed orthodontic appliance to move a patient's teeth according to a treatment plan. This example also describes the characteristics that the orthodontic appliance can have following its use, in contrast to its characteristics prior to use.

A patient in need of, or desirous of, a therapeutic treatment to rearrange at least one tooth has their teeth arrangement assessed. An orthodontic treatment plan is generated for the patient. The orthodontic treatment plan comprises a plurality of intermediate tooth arrangements for moving teeth along a treatment path, from the initial arrangement (e.g., that which was initially assessed) toward a final arrangement. The treatment plan includes the use of an orthodontic appliance, fabricated using the resins and methods disclosed further herein, to provide orthodontic appliances having a plurality of polymer phases. In some embodiments, a plurality of orthodontic appliances are used, each of which can be fabricated using the resins and methods disclosed further herein.

The orthodontic appliances are provided, and iteratively applied to the patient's teeth to move the teeth through each of the intermediate tooth arrangements toward the final arrangement. The patient's tooth movement is tracked. A comparison is made between the patient's actual teeth arrangement and the planned intermediate arrangement. Where the patient's teeth are determined to be tracking according to the treatment plan, but have not yet reached the final arrangement, the next set of appliances can be administered to the patient. The threshold difference values of a planned position of teeth to actual positions selected as indicating that a patient's teeth have progressed on-track are provided above in Table 1. If a patient's teeth have progressed at or within the threshold values, the progress is considered to be on-track. Favorably, the use of the appliances disclosed herein increases the probability of on-track tooth movement.

The assessment and determination of whether treatment is on-track can be conducted, for example, 1 week (7 days) following the initial application of an orthodontic appliance. Following this period of application, additional parameters relating to assessing the durability of the orthodontic appliance can also be conducted. For example, relative repositioning force (compared to that which was initially provided by the appliance), intactness of polymer chains (e.g., the percent of polymer chains that are not broken), relative flexural modulus, and relative elongation at break can be determined.

What is claimed is:

1. An orthodontic appliance comprising a polymeric material obtainable by curing a composition comprising:

a compound having the structure of Formula (I), or a salt or solvate thereof:

(I)

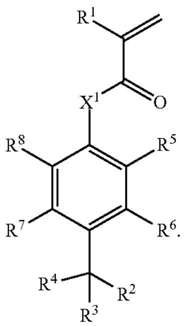

wherein:

$R^1$ is H, halogen, $C_1$-$C_6$ alkyl, $C_1$-$C_6$ alkenyl, $C_1$-$C_6$ alkynyl, $C_1$-$C_6$ cycloalkyl, $C_1$-$C_6$ heterocycloalkyl, —$OR^9$, or —$N(R^9)_2$;

each instance of $R^2$, $R^3$, and $R^4$ is independently selected from the group consisting of $C_1$-$C_6$ alkyl, $C_1$-$C_6$ alkenyl, $C_1$-$C_6$ alkynyl, $C_1$-$C_6$ cycloalkyl, $C_1$-$C_6$ heterocycloalkyl, —$OR^9$, and —$N(R^9)_2$; or optionally any two of $R^2$, $R^3$, and $R^4$ are taken together along with the carbon to which they are commonly attached to form $C_1$-$C_8$ cycloalkyl or $C_1$-$C_8$ heterocycloalkyl; or optionally $R^2$, $R^3$, and $R^4$ are taken together along with the carbon to which they are commonly attached to form a caged ring;

$R^5$, $R^6$, $R^7$, and $R^8$ are each independently selected from the group consisting of H, halogen, $C_1$-$C_6$ alkyl, $C_1$-$C_6$ alkenyl, $C_1$-$C_6$ alkynyl, —$OR^9$, —$N(R^9)_2$, —(C═O)—$R^9$, —O—(C═O)—$R^9$, and —($NR^9$)—(C═O)—$R^9$;

each instance of $R^9$ is independently selected from the group consisting of H, $C_1$-$C_6$ alkyl, $C_1$-$C_6$ alkenyl, and $C_1$-$C_6$ alkynyl;

each instance of $R^1$, $R^2$, $R^3$, $R^4$, $R^5$, $R^6$, $R^7$, and $R^8$ is independently optionally substituted with one or more instances of $R^{10}$; and each instance of $R^{10}$ is independently selected from the group consisting of ═O, halogen, $C_1$-$C_4$ alkyl, $C_1$-$C_4$ alkenyl, $C_1$-$C_4$ alkynyl, —$OR^9$, —$N(R^9)_2$, —(C═O)—$R^9$, —O—(C═O)—$R^9$, and —($NR^9$)—(C═O)—$R^9$; and $X^1$ is $C(R^9)_2$, $NR^9$, O or S; and an oligomer comprising a glass transition temperature (Tg) of at most −10° C.

2. The orthodontic appliance of claim 1, wherein the composition comprises between about 10% and about 50% of the oligomer by weight.

3. The orthodontic appliance of claim 1, wherein the composition comprises between about 40% and 80% of the compound of Formula (I) elaim 1 by weight.

4. The orthodontic appliance of claim 1, further comprising a crosslinker.

5. The orthodontic appliance of claim 4, wherein the crosslinker comprises polytetrahydrofuran (PTHF).

6. The orthodontic appliance of claim 4, wherein the composition comprises between about 4% and 16% of the crosslinker.

7. The orthodontic appliance of claim 1, further comprising a photoinitiator.

8. The orthodontic appliance of claim 1, wherein upon curing the polymeric material comprising at least one property selected from the group consisting of:

a Young's modulus at 1.7 mm/min of between 800 and 1500 megapascals (MPa);

a Young's modulus at 510 mm/min of between 1200 and 2000 MPa;

an elongation at break at 1.7 mm/min of between 60% and 200%;

an elongation at break at 510 mm/min of between 10% and 120%;

a yield stress at 1.7 mm/min of between 24 and 35 MPa;

a yield stress at 510 mm/min of between 35 and 55 MPa;

a 24 hour force of between 1.3 and 3.0 Newtons (N); and a glass transition temperature of between 9° and 160° C.

9. The orthodontic appliance of claim 1, wherein $R^1$ is H, $C_1$-$C_6$ alkyl, $C_1$-$C_6$ alkenyl, or $C_1$-$C_6$ alkynyl, $C_1$-$C_6$ cycloalkyl, or $C_1$-$C_6$ heterocycloalkyl.

10. The orthodontic appliance of claim 1, wherein each instance of $R^2$, $R^3$, and $R^4$ is independently selected from the group consisting of $C_1$-$C_6$ alkyl, $C_1$-$C_6$ alkenyl, or $C_1$-$C_6$ alkynyl.

11. The orthodontic appliance of claim 1, wherein $R^2$, $R^3$, and $R^4$ are taken together along with the carbon to which they are commonly attached to form a caged ring.

12. The orthodontic appliance of claim 1, wherein $R^2$, $R^3$, and $R^4$ are taken together along with the carbon to which they are commonly attached to form

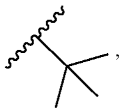, 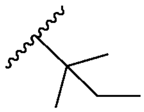, 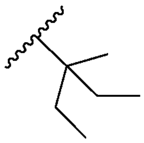,

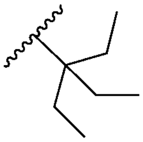, 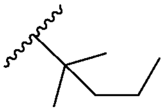,

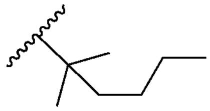, 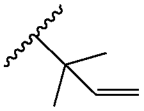,

-continued

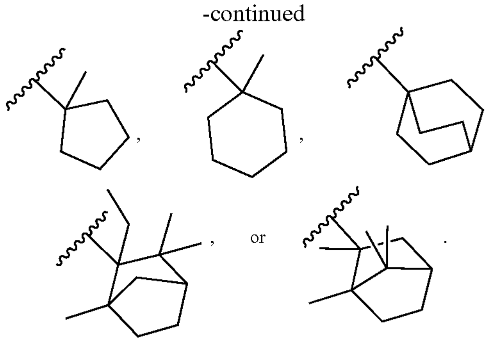

, or .

13. The orthodontic appliance of claim 1, wherein $R^5$, $R^6$, $R^7$, and $R^8$ are each H or —$OR^9$.

14. The orthodontic appliance of claim 1, wherein $R^6$ and $R^7$ are H.

15. The orthodontic appliance of claim 1, wherein the compound has the structure of Formula (Ib):

(Ib)

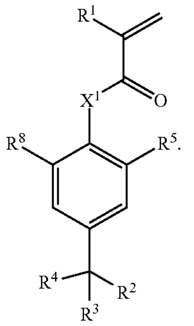

16. The orthodontic appliance of claim 1, wherein the compound is liquid or crystalline at room temperature and 1 atmosphere pressure.

17. The orthodontic appliance of claim 1, wherein the compound comprises a vapor pressure of less than 500 pascals (Pa) at 60° C.

18. The orthodontic appliance of claim 1, wherein the orthodontic appliance is a dental aligner, a dental expander, or a dental spacer.

19. An orthodontic appliance comprising a polymeric material obtainable by curing a composition comprising:

a compound having the structure of Formula (I), or a salt or solvate thereof:

(I)

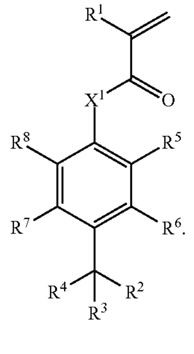

wherein:

$R^1$ is H, halogen, $C_1$-$C_6$ alkyl, $C_1$-$C_6$ alkenyl, $C_1$-$C_6$ alkynyl, $C_1$-$C_6$ cycloalkyl, $C_1$-$C_6$ heterocycloalkyl, —$OR^9$, or —$N(R^9)_2$;

any two of $R^2$, $R^3$, and $R^4$ are taken together along with the carbon to which they are commonly attached to form $C_1$-$C_8$ cycloalkyl or $C_1$-$C_8$ heterocycloalkyl; or $R^2$, $R^3$, and $R^4$ are taken together along with the carbon to which they are commonly attached to form a caged ring;

$R^5$, $R^6$, $R^7$, and $R^8$ are each independently selected from the group consisting of H, halogen, $C_1$-$C_6$ alkyl, $C_1$-$C_6$ alkenyl, $C_1$-$C_6$ alkynyl, —$OR^9$, —$N(R^9)_2$, —(C═O)—$R^9$, —O—(C═O)—$R^9$, and —($NR^9$)—(C═O)—$R^9$;

each instance of $R^9$ is independently selected from the group consisting of H, $C_1$-$C_6$ alkyl, $C_1$-$C_6$ alkenyl, and $C_1$-$C_6$ alkynyl;

each instance of $R^1$, $R^2$, $R^3$, $R^4$, $R^5$, $R^6$, $R^7$, and $R^8$ is independently optionally substituted with one or more instances of $R^{10}$, and each instance of $R^{10}$ is independently selected from the group consisting of ═O, halogen, $C_1$-$C_4$ alkyl, $C_1$-$C_4$ alkenyl, $C_1$-$C_4$ alkynyl, —$OR^9$, —$N(R^9)_2$, —(C═O)—$R^9$, —O—(C═O)—$R^9$, and —($NR^9$)—(C═O)—$R^9$ $X^1$ is $C(R^9)_2$, $NR^9$, O or S; and an oligomer comprising a glass transition temperature ($T_g$) of at most −10° C.

20. The orthodontic appliance of claim 19, wherein $R^2$, $R^3$, and $R^4$ are taken together along with the carbon to which they are commonly attached to form

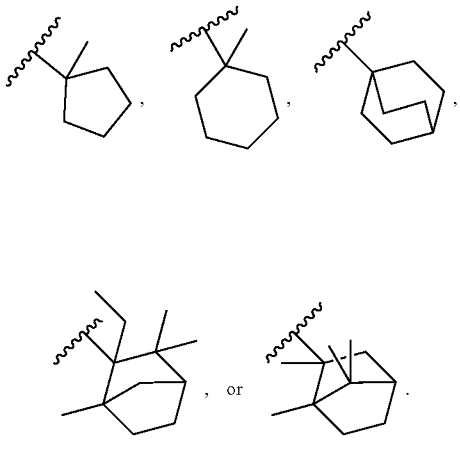

, or .

* * * * *